United States Patent [19]

Barton et al.

[11] Patent Number: 5,563,115
[45] Date of Patent: Oct. 8, 1996

[54] HERBICIDAL COMPOUNDS

[75] Inventors: John E. D. Barton; David Cartwright, both of Reading; John M. Cox, Wokingham; Glynn Mitchell, Iver, all of England; Charles G. Carter, Silver Spring, Md.; David L. Lee, Martinez, Calif.; Francis H. Walker, Mill Valley, Calif.; Frank X. Woolard, Pt. Richmond, Calif.

[73] Assignee: Zeneca Limited, London, England

[21] Appl. No.: 453,916

[22] Filed: May 30, 1995

Related U.S. Application Data

[62] Division of Ser. No. 102,004, Aug. 4, 1993, Pat. No. 5,426,091, which is a division of Ser. No. 819,080, Jan. 10, 1992, Pat. No. 5,250,501, which is a division of Ser. No. 595,710, Oct. 9, 1990, Pat. No. 5,098,464, which is a continuation of Ser. No. 170,389, Mar. 18, 1988, abandoned.

[30] Foreign Application Priority Data

| Mar. 19, 1987 | [GB] | United Kingdom | 8706557 |
| Mar. 21, 1987 | [GB] | United Kingdom | 8712037 |
| May 21, 1987 | [GB] | United Kingdom | 8712038 |
| Jun. 26, 1987 | [GB] | United Kingdom | 8715044 |
| Dec. 14, 1987 | [GB] | United Kingdom | 8729108 |

[51] Int. Cl.$^6$ .............. C07D 401/04; C07D 409/14; C07D 405/04; A01N 43/72; A01N 43/92
[52] U.S. Cl. .............. 504/288; 548/468; 548/465; 549/59; 546/242; 546/281.1; 546/284.4; 546/280.4; 546/278.1; 546/280.1; 546/279.7; 546/281.4; 546/281.7; 546/282.1; 546/284.7; 546/22; 504/254
[58] Field of Search ............... 504/288, 254; 548/468, 465; 549/59; 546/242, 273, 274

[56] References Cited

U.S. PATENT DOCUMENTS

| 4,008,249 | 2/1977 | Fischer et al. | 71/92 |
| 4,063,925 | 12/1977 | Konotsune et al. | 71/92 |
| 4,406,688 | 9/1983 | Konno et al. | 71/92 |
| 4,643,757 | 2/1987 | Baba et al. | 71/92 |
| 4,687,858 | 8/1987 | Konotsune et al. | 71/92 |
| 5,053,414 | 10/1991 | Toda et al. | 548/200 |

FOREIGN PATENT DOCUMENTS

| 0047602 | 4/1980 | Japan | 71/92 |
| 0073660 | 6/1980 | Japan | 71/92 |
| 0188572 | 11/1982 | Japan | 71/92 |
| 0034949 | 2/1985 | Japan | 548/378 |
| 2002375 | 2/1979 | United Kingdom | 71/92 |

Primary Examiner—David B. Springer
Attorney, Agent, or Firm—Cushman Darby & Cushman, L.L.P.

[57] ABSTRACT

A compound of formula (I):

$$\text{(I)}$$

or a salt, enamine or the like, acylate, sulphonate, carbamate or ether derivative thereof; wherein X, $X^1$ and $X^2$ are independently oxygen or sulphur, $R^1$ is an optionally substituted heterocyclic or cycloalkyl group, and Y is an optionally substituted $C_2$–$C_4$ alkylene group which is optionally interposed by an oxygen atom, a group $$\diagdown_{S(O)_p}\diagup$$

a group $$\diagdown_{P(O)_s}^{R^b}\diagup$$

or an optionally mono-substituted nitrogen atom, wherein p is 0, 1 or 2, s is 0 or 1 and $R^b$ is alkyl or alkoxy; provided that when X, $X^1$ and $X^2$ are oxygen, $R^1$ is not pyridyl or pyrimidinyl. Processes for the preparation of these compounds and herbicidal compositions containing them are also described and claimed.

7 Claims, No Drawings

1

HERBICIDAL COMPOUNDS

This is a division of application Ser. No. 08/102,004, filed Aug. 4, 1993, now U.S. Pat. No. 5,426,091, which is a division of application Ser. No. 07/819,080, filed Jan. 10, 1992, now U.S. Pat. No. 5,250,501, which is a division of application Ser. No. 07/595,710, filed Oct. 9, 1990, now U.S. Pat. No. 5,098,464, which is a continuation of application Ser. No. 07/170,389, filed Mar. 18, 1988, now abandoned.

The present invention relates to certain herbicidally active substituted cyclic diones, to processes for their preparation and to compositions containing them.

Herbicidal compounds containing a cyclohexane dione coupled to an aryl group are described and claimed for example in EP-A-90262, EP-A-137,963, EP-A-135,191 and EP-A-186119.

According to the present invention there is provided a compound of formula (I):

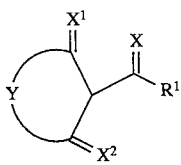
(I)

or a salt, enamine or the like, acylate, sulphonate, carbamate or ether derivative thereof; wherein X, X$^1$ and X$^2$ are independently oxygen or sulphur; R$^1$ is an optionally substituted heterocyclic or cycloalkyl group; and Y is optionally substituted C$_2$–C$_4$ alkylene group which is optionally interposed by an oxygen atom, a group

a group

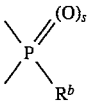

or an optionally mono-substituted nitrogen atom, wherein p is 0, 1 or 2, s is 0 or 1 and R$^b$ is alkyl or alkoxy; provided that when X, X$^1$ and X$^2$ are oxygen, R$^1$ is not pyridyl or pyrimidinyl.

Compounds of formula (I) can exist in a number of tautomeric forms, for example:

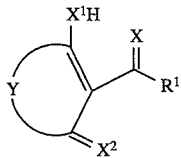

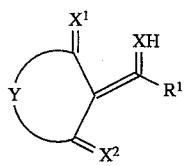

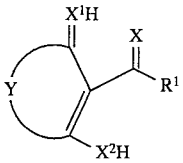

wherein R$^1$, X, X$^1$, X$^2$ and Y are as defined in relation to formula (I). Further tautomers exist when Y contains a hydrogen substituent on a carbon atom adjacent to the carbon bearing X$^1$ or X$^2$. It is intended that all such forms are included within the scope of the invention.

When the compound contains a free hydroxy or thiol group in this way, it may be derivatised to form salts, in particular agriculturally acceptable salts, enamines or the like, acylates, sulphonates, carbamates or ethers.

Suitable agriculturally acceptable salts include salts such as sodium, potassium, calcium and ammonium salts.

Examples of ammonium salts include salts with ions of formula N$^+$R$^c$R$^d$R$^e$R$^f$ where R$^c$, R$^d$, R$^e$ and R$^f$ are independently selected from hydrogen and C$_{1-10}$ alkyl optionally substituted by, for example, hydroxy. Suitably when any of R$^c$, R$^d$, R$^e$ or R$^f$ are optionally substituted alkyl, they contain from 1 to 4 carbon atoms.

Suitable acylate or ether derivatives are compounds wherein the OH moiety has been converted to a group of formula —OCOR$^2$ or —OR$^2$ respectively wherein R$^2$ is optionally substituted alkyl having for example from 1 to 6 carbon atoms, or aryl such as phenyl.

Suitable carbamate derivatives are compounds wherein the OH moiety has been converted to a group

wherein R$^3$ and R$^4$ are independently hydrogen or a group R$^2$ as defined above.

Preferably X, X$^1$ and X$^2$ are oxygen.

As used herein the term "enamine or the like" refers to derivatives where one of X or X$^1$ is oxygen and the other is replaced by NR$^3$R$^4$, halo such as fluoro or SR$^2$.

These derivatives can be prepared by conventional methods.

Suitable heterocyclic groups R$^1$ include mono- or fused bicyclo- heterocyclic rings which may be aromatic or non-aromatic. Suitably R$^1$ includes up to ten ring atoms up to five preferably three of which may be selected from oxygen, nitrogen and sulphur.

When R$^1$ is a monocyclic ring, it is suitably a heteroaryl group having up to 7 ring atoms up to 3 of which are selected from oxygen, nitrogen and sulphur. As used here in the term "heteroaryl" means aromatic heterocyclic.

When R$^1$ is a fused bicyclic ring, one or both of the rings may contain heteroatoms and it may be bonded to the group

by way of either of these rings.

Examples of such heterocyclic groups including furyl, thienyl, pyrrolyl, pyrazolyl, pyridyl, pyrimidinyl, imidazoyl, triazolyl, dithiol, oxathiol, isoxazolyl, oxazolyl, thiazolyl, isothiazolyl, oxadiazolyl, thiodiazolyl, oxatriazolyl, dioxazolyl, oxathiazolyl, oxathiol, dioxinyl, pyridazinyl, pyrazinyl, piperazinyl, priazinyl, oxazinyl, isoxazinyl, oxathiazinyl, morphlinyl, azepinyl, oxepinyl, thiepinyl, diazepinyl, benzofuranyl, isobenzofuranyl, benzothienyl, isobenzothienyl, thionaphthalenyl, isothionaphthalenyl, indolyl, isoindolyl, indazolyl, indoleninyl, isobenzazolyl, pyranopyrrolyl, isoindazolyl, indoxazinyl, benzoxazolyl, benzopyranyl, quinolinyl, isoquinolinyl, cinnolinyl, phthalazinyl, quinoxalinyl, quinazolinyl, naphthyridinyl, pyridopyridinyl, pyranyl, thiopyranyl, chromenyl, thiachromenyl, benzoxazinyl, benzisoxazinyl and purine.

Particular examples of heterocyclic groups $R^1$ include furyl, thiazolyl, thienyl, benzoxazolyl, pyrazolyl, pyridazinyl, pyrazinyl, benzoxazolyl.

These heterocycles may be linked either through carbon atom or when possible through a nitrogen atom.

Suitable cycloalkyl groups $R^1$ contain up to 10 ring carbon atoms, preferably up to 7 ring atoms.

Suitable optional substituents for the groups $R^1$ and $R^8$ include one or more groups selected from oxo, mercapto, halo, such as fluoro, chloro, bromo or iodo, nitro, cyano, amino, mono or dialkylamino, amido, alkyl, alkenyl, alkynyl, cycloalkyl, haloalkyl such as trifluoromethyl, haloalkoxy such as trifluoromethoxy, optionally substituted aryl such as phenyl or naphthyl, hydroxy, alkoxy, alkoxycarbonyl, alkylcarbonyl, mono- or dialkylcarbamoyl, alkylthio, alkylsulphinyl, alkylsulphonyl, sulphonamido, alkylcarbonyloxy, alkylcarbonylamino or heterocyclyl such as pyridyl and thienyl.

The substituents may be attached to a carbon and/or nitrogen atom of the group $R^1$.

In the above-mentioned list of substituents, the alkyl, alkenyl or alkynyl groups or moieties preferably contain from 1 to 6 carbon atoms. Suitable optional substituents for the aryl groups include halo such as fluoro, chloro or bromo, $C_{1-6}$ alkyl or $C_{1-6}$ alkoxy.

In a preferred embodiment, is a 6-membered heteroaryl ring for example from one or two nitrogen atoms such as pyridyl, pyrimidinyl, pyridazinyl or pyrazinyl.

In another preferred embodiment, $R^1$ is a five membered heteroaryl group or comprises a five-membered heteroaryl group.

For example, $R^1$ is selected from groups of formula:

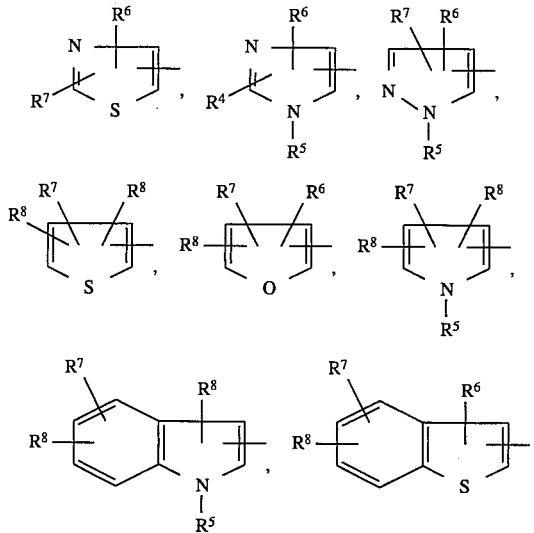

wherein $R^5$ is hydrogen or $C_1$–$C_4$ alkyl, preferably $C_1$–$C_2$ alkyl or optionally substituted aryl such as phenyl; $R^6$, $R^7$ and $R^8$ independently are (1) hydrogen; (2) halogen, preferably chlorine, fluorine or bromine; (3) $C_1$–$C_4$ alkyl, preferably methyl; (4) haloalkoxy, preferably $OCF_3$; (5) $C_1$–$C_4$ alkoxy, preferably methoxy; (6) cyano; (7) nitro; (8) $C_1$–$C_4$ haloalkyl, preferably trifluoromethyl; (9) $R^9SOn$— wherein n is the integer 0, 1, or 2, preferably 2; and $R^9$ is (a) $C_1$–$C_4$ alkyl, preferably methyl;

(b) $C_1$–$C_4$ alkyl substituted with halogen, cyano, $C_1$–$C_2$ alkoxy or $C_1$–$C_2$ alkylthio, preferably chloromethyl, difluoromethyl, trifluoromethyl or cyanomethyl;

(c) phenyl; or (d) benzyl; (10) —$NR^{10}R^{11}$ wherein $R^{10}$ and $R^{11}$ independently are hydrogen or $C_1$–$C_4$ alkyl; (11) $R^{12}C(O)$— wherein $R^{12}$ is $C_1$–$C_4$ alkyl or $C_1$–$C_4$ alkoxy; (12) —$SO_2NR^{10}R^{11}$ wherein $R^{10}$ and $R^{11}$ are as defined above; or (13) —$N(R^{10})C(O)R^{11}$ wherein $R^{10}$ and $R^{11}$ are as defined above.

In particular $R^1$ is a group of formula:

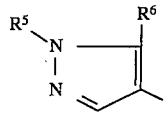

wherein $R^5$ and $R^6$ are as defined above.

In particular $R^5$ is $C_{1-6}$ alkyl which may be straight or branched or optionally substituted phenyl, such as phenyl, p-chlorophenyl, p-methoxyphenyl or p-methylphenyl.

Preferred groups $R^6$ are haloalkyl in particular trifluoromethyl.

In a further preferred embodiment $R^1$ is a bicyclic group of formula

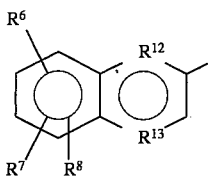

wherein $R^6$, $R^7$ and $R^8$ are as defined above;

One of $R^{12}$ or $R^{13}$ is —N= and the other is $C(R^{14})$ wherein $R^{14}$ is hydrogen, halogen, such as chlorine, fluorine or bromine; $C_1$–$C_4$ alkyl, such as methyl; $OCF_3$; $C_1$–$C_4$ alkoxy, such as methoxy; cyano; nitro; $C_1$–$C_4$ haloalkyl, such as trifluoromethyl; $R^{15}SOm$ wherein m is the integer 0, 1 or 2, preferably 2; and $R^{15}$ is $C_1$–$C_4$ alkyl, such as methyl.

In addition $R^1$ may be a bicyclic group of sub formula

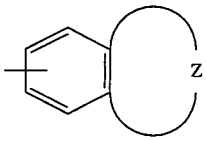

wherein Z is a five or six membered saturated or unsaturated fused ring containing up to three heteroatoms selected from oxygen, sulphur and nitrogen. Preferably the ring Z contains two oxygen atoms or an oxygen or sulphur and a nitrogen atom. Thus examples of the group $R^1$ include

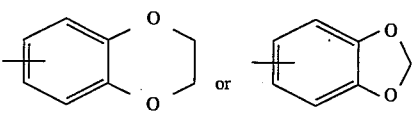

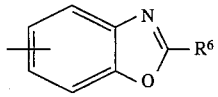

where $R^6$ is as defined above. Suitable optional substituents for the group Y include those listed above for $R^1$. In addition substituents on adjacent carbon atoms in the group Y may be joined together to form a fused ring system. The fused ring may be aromatic or non-aromatic and may be optionally substituted by one or more substituents listed above for $R^1$. For example, the group

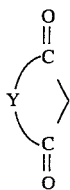

may be the group:

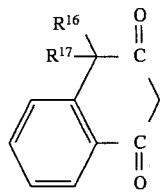

Preferably Y is a group of formula:

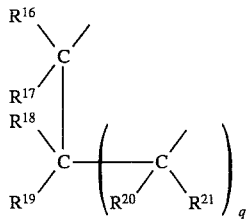

wherein $R^{16}$, $R^{17}$, $R^{18}$, $R^{19}$, $R^{20}$ and $R^{21}$ and are independently selected from hydrogen, $C_1$–$C_4$ alkyl, $C_1$–$C_4$ alkanoyl or —$CO_2R^{22}$ wherein $R^{22}$ is $C_{1-4}$ alkyl or $R^{16}$ and $R^{17}$ or $R^{18}$ and $R^{19}$ or $R^{20}$ and $R^{21}$ together with the carbon atom to which they are attached form a $C_{3-6}$ cycloalkyl ring; and q is 0 or 1. Most preferably q is 1.

Other examples of the group Y are

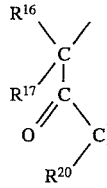 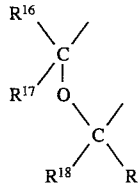 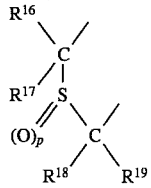

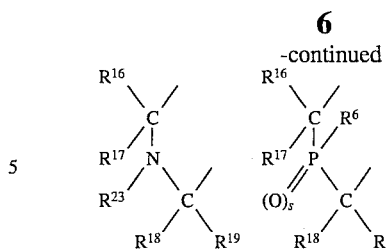

wherein $R^{16}$, $R^{17}$, $R^{18}$, $R^{19}$, $R^{20}$, $R^b$, s and p are as hereinbefore defined and $R^{23}$ is alkyl or alkoxy preferably having up to 6 carbon atoms.

In particular the group

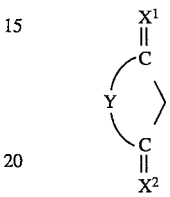

is a group of formula

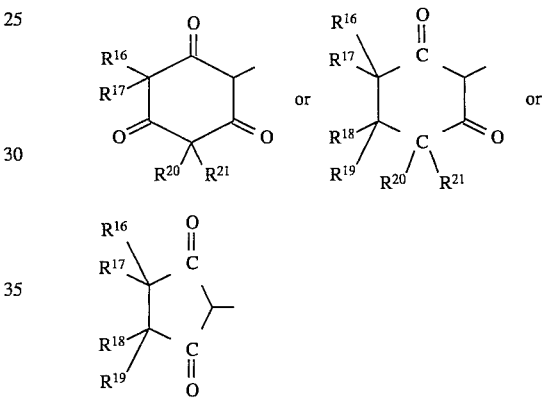

A suitable alkanoyl group for $R^{16}$, $R^{17}$, $R^{18}$, $R^{19}$, $R^{20}$ and $R^{21}$ is acetyl.

Preferably only one of $R^{16}$, $R^{17}$, $R^{18}$, $R^{19}$, $R^{20}$ and $R^{21}$ is either alkanoyl or —$CO_2R^2$.

Preferably $R^{16}$, $R^{17}$, $R^{18}$, $R^{19}$, $R^{20}$ and $R^{21}$ are hydrogen or $C_{1-4}$ alkyl in particular $C_{1-2}$ alkyl.

Most preferably $R^{16}$, $R^{17}$, $R^{18}$, $R^{19}$, $R^{20}$ $R^{21}$ hydrogen or methyl.

A particularly preferred sub-group of compounds are compound of formula (IA):

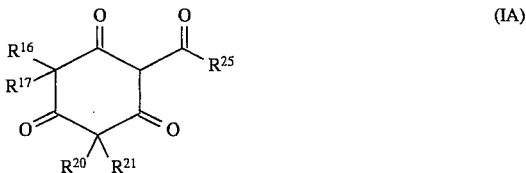

(IA)

or a salt, acylate or sulphonate derivative thereof; wherein $R^{25}$ is an optionally substituted heteroaryl group, $R^{16}$, $R^{17}$, $R^{20}$ and $R^{21}$ are as hereinbefore defined, provided that at least $R^{16}$ and $R^{17}$ or $R^{20}$ and $R^{21}$ are not both hydrogen and that not more than two of $R^{16}$, $R^{17}$, $R^{20}$ and $R^{21}$ are $C_{1-4}$ alkanoyl or —$CO_2R^{22}$.

Most preferably $R^{16}$, $R^{17}$, $R^{20}$ and $R^{21}$ are $C_{1-4}$ alkyl in particular methyl.

Examples of compounds of formula (I) are set out in Tables I and II.

TABLE I

Structure: R¹–C(=O)–[cyclohexane-1,3-dione with substituents R16, R17 at one carbon, R18, R19 at next, R20, R21 at next]

| Compound NO. | R¹ | R16 | R17 | R18 | R19 | R20 | R21 | CHARACTERISING DATA |
|---|---|---|---|---|---|---|---|---|
| 1 | 5-methylthiophen-2-yl | H | H | $CH_3$ | $CH_3$ | H | H | $M^+$ 250 δ 8.14(d, 1); 7.70 (d, 1); 7.12(dd, 1); 2.54 (broad s, 4); 1.12(s, 6); 1760(broad s, 1). |
| 2 | 5-methylthiophen-2-yl | H | H | H | H | H | H | $M^+$ 222 δ 8.06(d, 1); 7.68 (d, 1); 7.10(dd, 1); 2.64 (broad s, 4); 2.04(M, 2); 1730(broad s, 1). |
| 3 | 3,5-dichloro-4-methylthiophen-2-yl (with methyl) | H | H | $CH_3$ | $CH_3$ | H | H | $MH^+$ 319, $(M-Cl)^+$ 283 δ 6.80(s, 1); 2.64(s, 2); 2.40(s, 2); 1.12(s, 6); 16.75(s, 1) all peaks broad. |
| 4 | 3,5-dichloro-4-methylthiophen-2-yl | H | H | H | H | H | H | $MH^+$ 291, $(M-Cl)^+$ 255 δ 6.80(s, 1); 2.74(t, 2); 2.50(t, s); 2.04(M, 2); 16.94(s, 1). |
| 5 | 5-bromo-3-methylthiophen-2-yl (methyl) | H | H | $CH_3$ | $CH_3$ | H | H | $M^+$ 330 δ 8.0(d, 1); 7.12 (d, 1); 2.54(broad s, 4); 1.12(s, 6). |
| 6 | 3-methylthiophen-2-yl | H | H | H | H | H | H | $M^+$ 236, $M^+$–$CH_3$ 221 δ 7.46 (d, 1); 6.87(d, 1); 2.61(broad, 4), 2.06(M, 2); 16.6(broad s, 1). |
| 7 | 3-chloro-6-methylpyridazin-yl | $CH_3$ | $CH_3$ | H | H | H | H | H-NMR(CDCl$_3$); δ 1.31 (s, 2 $CH_3$), 1.91(s, $CH_3$), 2.71(t, $CH_2$), 7.62(s 2 ar.H); MS: 168, 170, 196, 198, 224, 226, 280, ($M^+$), 282 |
| 8 | chloro-methylpyrazinyl | $CH_3$ | $CH_3$ | H | H | H | H | H-NMR(CDCl$_3$); δ 1.06(s, $CH_3$), 1.23(s, $CH_3$), 1.85(t, $CH_2$), 2.61(t, $CH_2$), 8.45(s, ar.H), 8.50(s, ar.H); MS: 113, 128, 130, 141, 143, 168, 170, 196, 198, 209, 211, 224, 226, 265, 267, 280($M^+$), 282 |
| 9 | 5-chloro-thiophen-2-yl | H | H | H | H | H | H | H-NMR(CDCl$_3$); δ 2.09(m, $CH_2$), 2.67(br.s, 2$CH_2$), 7.00 (d, ar. H), 8.06(d, ar. H), 15.13(br.s, OH); MS: 145, 147, 200, 202, 221, 256 ($M^+$), 258 |
| 10 | 5-chloro-thiophen-2-yl | $CH_3$ | $CH_3$ | H | H | H | H | H-NMR(CDCl$_3$); δ 1.31, 1.67 (s, 2$CH_3$), 1.92(t, $CH_2$), 2.73 (t, $CH_2$), 7.13(d, ar. H)8.1 (d, ar.H); MS: 145, 147, 162, 164, 200, 202, 228, 284($M^+$), 286 |

TABLE I-continued

Structure: $R^1-C(=O)-$ attached to a cyclohexane-1,3-dione ring with substituents $R^{16}, R^{17}$ on one carbon, $R^{18}, R^{19}$ on the next, and $R^{20}, R^{21}$ on the carbon between the two carbonyls.

| Compound NO. | R¹ | R¹⁶ | R¹⁷ | R¹⁸ | R¹⁹ | R²⁰ | R²¹ | CHARACTERISING DATA |
|---|---|---|---|---|---|---|---|---|
| 11 | 2,3-dimethylthien-2-yl (3-CH₃, 2-linked thiophene) | CH₃ | CH₃ | H | H | H | H | H-NMR(CDCl₃): δ 1.37(s, 2CH₃), 1.88(t, CH₂), 2.38(s, CH₃), 2.69(t, CH₂), 6.92(d, ar.H), 7.47(d, ar.H) 7.47(d, ar.H); MS: 125, 138, 167, 249, 264 M⁺) |
| 12 | 5-methylthien-2-yl | H | H | H | H | H | H | H-NMR(CDCl₃): δ 2.01(m, CH₂). 2.49(s, CH₃), 2.68(br.m. 2CH₂), 6.81(d, ar.H), 7.98 (d, ar.H), 17.0(br.s. OH): MS: 125, 152, 180, 236 (M⁺) |
| 13 | 5-methylthien-2-yl | CH₃ | CH₃ | H | H | H | H | H-NMR(CDCl₃): δ 1.22(s, 2CH₃), 1.83(t, CH₂, 2.52(s, CH₃), 2.68(t, CH₂), 6.72(d, ar.H), 7.82(d, ar.H); MS: 125, 152, 180, 193, 208, 264(M⁺) |
| 14 | 4,5-dibromothien-2-yl | H | H | H | H | H | H | H-NMR(CDCl₃): δ 1.99(m, CH₂), 2.62(t, 2CH₂), 8.02(s, ar.H), 17.33(br.s, OH); MS: 220, 267, 269, 271, 299, 301, 378(M⁺), 380, 382 |
| 15 | 4,5-dibromothien-2-yl | CH₃ | CH₃ | H | H | H | H | H-NMR(CDCl): δ 1.28 (s, 2CH₃), 1.87(t, CH₂), 2.75(br. t. CH₂) 8.00(s, ar.H); MS: 139, 267, 269, 271, 322, 324, 326, 327, 328, 329, 350, 352, 354, 406 (M⁺), 408, 410 |
| 16 | 3-chlorobenzo[b]thien-2-yl | H | H | H | H | H | H | H-NMR(CDCl₃+DMSO-d₆): δ 2.08 (m. CH₂), 2.52(t, 2CH₂), 7.40 8.01(m, 4 ar.H); MS: 195, 242, 271(M⁺—Cl) |
| 17 | 3-chlorobenzo[b]thien-2-yl | CH₃ | CH₃ | H | H | H | H | H-NMR(CDCl₃): δ 1.26(s, 2CH₃), 1.90(t, CH₂), 2.72(t, CH₂), 7.41(m, 2 ar.H), 7.81 (m, 2ar.H); MS: 195, 242, 299 (M⁺—Cl) |
| 18 | 2,5-dichloro-3-methylthien-4-yl | CH₃ | CH₃ | H | H | H | H | H-NMR(CDCl₃): δ 1.27 (s, 2CH₃), 1.88(t, CH₂), 2.68(t, CH₂), 6.68(s, ar. H); MS: 179, 181, 226, 228, 265, 267, 283 (M⁺—Cl), 285, 287 |
| 19 | 3,4-dibromothien-2-yl | H | H | H | H | H | H | H-NMR(CDCl₃): δ 2.17(m, CH₂), 2.68(br.m, 2CH₂), 7.51 (s, ar.H); MS: 299(M⁺—Br), 301 |
| 20 | 3,5-dichlorothien-2-yl | H | H | H | H | H | H | H-NMR(CDCl₃): δ 2.06(m, CH₂), 2.62(br.m, 2CH₂), 7.41 (s, ar.H); MS: 179, 181, 226, 225 (M⁺—Cl), 257, 289(M⁺—H), 291 |
| 21 | 3,5-dichlorothien-2-yl | CH₃ | CH₃ | H | H | H | H | H-NMR(CDCl₃): δ 1.34(s, 2CH₃), 2.00(t, CH₂), 2.80(t, CH₂), 7.50(s, ar.H); MS: 179, 181, 199, 201, 265, 267, 283 (M⁺—Cl), 285, 317(M⁺—H), 319 |

TABLE I-continued

| Compound NO. | R¹ | R¹⁶ | R¹⁷ | R¹⁸ | R¹⁹ | R²⁰ | R²¹ | CHARACTERISING DATA |
|---|---|---|---|---|---|---|---|---|
| 22 | 5-nitro-2-furyl (O₂N–furan) | H | H | H | H | H | H | H-NMR(CDCl₃+DMSO-d₆): δ 2.17 (m, CH₂), 263, (t, 2CH₂), 7.52 (s. ar.H); MS: 139, 177, 205, 251(M⁺) |
| 23 | 5-nitro-2-furyl (O₂N–furan) | CH₃ | CH₃ | H | H | H | H | H-NMR(CDCl₃): δ 1.31(s, 2CH₃ₗ), 1.98(t, CH₂), 2.76(t, CH₂), 7.44(d, ar.H), 7.50(d, ar.H); MS: 167, 176, 195, 223, 233, 251, 279(M⁺), 280 |
| 24 | 1-methylpyrrol-2-yl | H | H | H | H | H | H | H-NMR(CDCl₃+DMSO-d6):δ 2.00 (m, CH₂), 2.45(t, 2CH₂), 3.85 (s, CH₃), 6.00(dd, ar.H), 6.68(dd, ar.H), 6.95(dd, ar.H); MS: 108, 139, 202, 219(M⁺) |
| 25 | 1-methylpyrrol-2-yl | H | H | CH₃ | CH₃ | H | H | H-NMR(CDCl₃): δ 1.14(s, 2CH₃), 2.42(s, 2CH₂), 3.90 (s,CH₃N), 6.15(dd, ar.H), 6.86 (m, 2 ar.H); MS: 108, 135, 167, 1230, 247(M⁺) |
| 26 | 1-methylindol-2-yl | H | H | H | H | H | H | H-NMR(CDCl₃): δ 2.10(m, CH₂), 2.58(br.m 2CH₂), 3.88 (s, CH₃N), 7.04(s, ar.H), 7.3–7.7(m, 4 ar.H); MS: 130, 131, 139, 144, 158, 269(M⁺) |
| 27 | 1-methylindol-2-yl | CH₃ | CH₃ | H | H | H | H | H-NMR(CDCl₃): δ 1.30(s, 2CH₃), 1.90(t, CH₂), 2.62(t, CH₂), 3.84(s, CH₃N), 6.88(s, ar.H), 7.00–7.6(m, 4 ar.H); MS: 130, 131, 158, 167, 185, 213, 241, 280, 297(M⁺) |
| 28 | 1-methylindol-2-yl | H | H | CH₃ | CH₃ | H | H | H-NMR(CDCl₃): δ 1.10(s, 2CH₃ₗ), 2.38(s, 2CH₂), 3.90(s, CH₃N), 6.90(s, ar.H), 7.00–7.55 (m, 4 ar.H); MS: 130, 131, 158, 167, 280, 297(M⁺) |
| 29 | 5-methylsulfonyl-1-methylpyrrol-2-yl (CH₃O₂S–pyrrole–CH₃) | CH₃ | CH₃ | H | H | H | H | H-NMR(CDCl₃): δ 1.23(s, 2CH₃ₗ), 1.91(t, CH₂), 2.70(t, CH₂), 3.16(s, CH₃SO₂), 4.03(s, CH₃N), 6.54(d, ar.H), 6.85(d, ar.H); MS: 159, 167, 172, 173, 186, 246, 325(M⁺) |
| 30 | 3-methylsulfonyl-5-acetyl-1H-pyrrol-2-yl (CH₃O₂S, CH₃C(O), pyrrole) | CH₃ | CH₃ | H | H | H | H | H-NMR(CDCl₃): δ 1.08(s, 2CH₃), 1.80 t, CH₂), 2.53(m, CH₂), 2.63(s, CH₃CO), 3.21(s, CH₃ SO₂), 3.80(s, CH₃N), 6.95 (s, ar.H); MS: 167, 186, 215, 228, 324, 367(M⁺) |
| 31 | quinoxalin-2-yl | CH₃ | CH₃ | H | H | H | H | H-NMR(CDCl₃): δ 1.16(s, 2CH₃), 1.97(t, CH₂), 2.68(t, CH₂), 7.8–8.15(m, 4ar.H), 8.97 (s, ar.H); MS: 129, 144, 156, 184, 212, 226, 240, 296(M⁺) |

TABLE I-continued

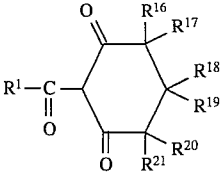

| Compound NO. | R¹ | R¹⁶ | R¹⁷ | R¹⁸ | R¹⁹ | R²⁰ | R²¹ | CHARACTERISING DATA |
|---|---|---|---|---|---|---|---|---|
| 32 | 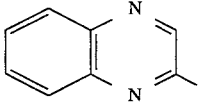 | H | H | CH₃ | CH₃ | H | H | H-NMR(CDCl₃): δ 1.10(s, 2CH₃), 2.50(s, 2CH₂), 7.81–8.17 (m, 4ar.H), 9.00(s, aR.H), 13.3 (br.s.OH); MS: 129, 130, 144, 156, 184, 212, 240, 296(M⁺) |
| 33 | 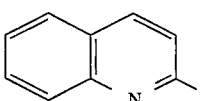 | CH₃ | CH₃ | H | H | H | H | H-NMR(CDCl₃): δ 1.15(s, CH₃), 1.27(s, CH₃), 2.00(m, CH₂), 2.76(m, CH₂), 7.7–8.8 (m 6 ar.H); MS: 128, 143, 156, 211, 239, 295(M⁺) |
| 34 | 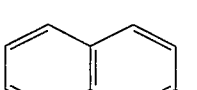 | H | H | H | H | H | H | MS: 128, 129, 143, 156, 173, 211, 267(M⁺) |
| 35 | 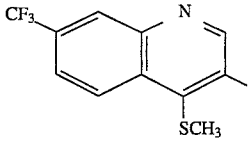 | H | H | H | H | H | H | mp. 110–130° C. |
| 36 | 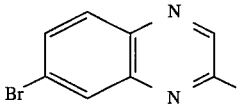 | H | H | H | H | H | H | H-NMR(CDCl₃): δ 2.2(m, CH₂), 2.7(br.m.2CH₂), 8.8.45 (m, 3ar.H), 8.95(s,ar.H); MS: 139, 149, 183, 208, 210, 318, 320, 346(M⁺), 348 |
| 37 | 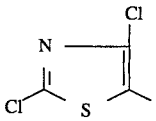 | H | H | H | H | H | H | H-NMR(CDCl₃): δ 2.10(m, CH₂), 2.66(t, 2CH₂), 13.70(br.s, OH); MS: 180, 182, 184, 227, 229, 256(M+—Cl), 258 |
| 38 | 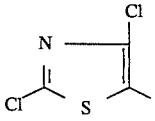 | CH₃ | CH₃ | H | H | H | H | H-NMR(CDCl₃): δ 1.32(s, 2CH₃), 1.98(t, CH₂), 2.80(t, CH₂); MS: 180, 182, 184, 227, 229, 255, 257, 284(M⁺—Cl), 286 |
| 39 | 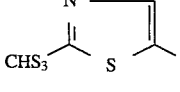 | H | H | H | H | H | H | H-NMR(CDCl₃): δ 2.05(m, CH₂), 2.58(t, 2CH₂), 2.63(s, CH₃S), 2.71(s, CH₃S); MS: 103, 139, 144, 177, 204, 268(M⁺—CH₃S) |
| 40 | 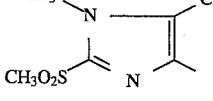 | H | H | H | H | H | H | H-NMR(CDCl₃): δ 2.10(m, CH₂), 2.18(s, CH₃), 2.61(m, 2CH₂), 3.40(s, CH₃SO₂), 3.95 (s, CH₃N); MS: 139, 174, 201, 233, 295, 297, 312(M⁺) |
| 41 | 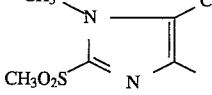 | CH₃ | CH₃ | H | H | H | H | H-NMR(CDCl₃): δ 1.30(s, 2CH₃, 1.91(t, CH₂), 2.19(s, CH₃), 2.71(t, CH₂), 3.38(s, CH₃SO₂), 3.92(s, CH₃N); MS: 167, 174, 187, 201, 325, 340(M⁺) |
| 42 | 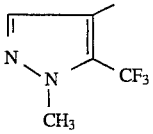 | H | H | H | H | H | H | H-NMR(CDCl₃L): δ 1.1–2.0 (br.m.2CH₂), 2.5(br.m.CH₂), 3.9(s, CH₃N), 7.9(s, ar.H); MS: 177, 219, 232, 269, 288(M⁺) |

TABLE I-continued

Structure: R¹-C(=O)- attached to cyclohexane-1,3-dione with substituents R¹⁶, R¹⁷ (on C adjacent to top C=O), R¹⁸, R¹⁹, R²⁰, R²¹

| Compound NO. | R¹ | R¹⁶ | R¹⁷ | R¹⁸ | R¹⁹ | R²⁰ | R²¹ | CHARACTERISING DATA |
|---|---|---|---|---|---|---|---|---|
| 43 | 1-methyl-5-CF₃-pyrazol-4-yl (N-CH₃) | $CH_3$ | $CH_3$ | H | H | H | H | H-NMR(CDCl₃): δ 1.13(br.s. 2CH₃), 1.78(t, CH₂), 2.6 (br.m.CH₂)(3.88(s, CH₃N), 7.85(s, ar.H); MS: 177, 232, 247, 260, 316(M⁺) |
| 44 | 1-phenyl-5-CF₃-pyrazol-4-yl | H | H | H | H | H | H | mp. 60–64° C. |
| 45 | 1-phenyl-5-CF₃-pyrazol-4-yl | $CH_3$ | $CH_3$ | H | H | H | H | glass |
| 46 | 1-ethyl-5-CF₃-pyrazol-4-yl | H | H | H | H | H | H | Semi solid |
| 47 | 1-ethyl-5-CF₃-pyrazol-4-yl | $CH_3$ | $CH_3$ | H | H | H | H | Semi solid |
| 48 | 1-t-butyl-5-CF₃-pyrazol-4-yl | H | H | H | H | H | H | Dark oil |
| 49 | 1-propyl-5-CF₃-pyrazol-4-yl | H | H | H | H | H | H | Oil |
| 50 | 1-propyl-5-CF₃-pyrazol-4-yl | $CH_3$ | $CH_3$ | H | H | H | H | Oil |

TABLE I-continued $$R^1-\underset{\underset{O}{\|}}{C}-\text{cyclohexane-1,3-dione with } R^{16}, R^{17}, R^{18}, R^{19}, R^{20}, R^{21}$$

| Compound NO. | R¹ | R¹⁶ | R¹⁷ | R¹⁸ | R¹⁹ | R²⁰ | R²¹ | CHARACTERISING DATA |
|---|---|---|---|---|---|---|---|---|
| 51 | 1-(4-chlorophenyl)-5-chloropyrazol-4-yl | H | H | H | H | H | H | mp 128–131° C. |
| 52 | 1-(4-chlorophenyl)-5-trifluoromethylpyrazol-4-yl | CH₃ | CH₃ | H | H | H | H | Glass |
| 53 | 1-(3,4-dichlorophenyl)-5-trifluoromethylpyrazol-4-yl | H | H | H | H | H | H | Mpt. 90–100° C. |
| 54 | 1-(4-methylphenyl)-5-trifluoromethylpyrazol-4-yl | H | H | H | H | H | H | Mpt 110–114° C. |
| 55 | 1-(4-methylphenyl)-5-trifluoromethylpyrazol-4-yl | CH₃ | CH₃ | H | H | H | H | Mpt 105–108° C. |

TABLE I-continued

Structure: R¹-C(=O)- attached to a cyclohexane-1,3-dione ring with substituents R16, R17, R18, R19, R20, R21

| Compound NO. | R¹ | R16 | R17 | R18 | R19 | R20 | R21 | CHARACTERISING DATA |
|---|---|---|---|---|---|---|---|---|
| 56 | 1-(4-methoxyphenyl)-4-trifluoromethyl-pyrazol-3-yl | H | H | H | H | H | H | Mpt. 112–115° C. |
| 57 | 1-(4-methoxyphenyl)-4-trifluoromethyl-pyrazol-3-yl | $CH_3$ | $CH_3$ | H | H | H | H | Mpt 71–76° C. |
| 58 | 5-chloro-2-methyl-thiophen-3-yl (2-Cl, 5-CH3 thienyl) | H | H | H | H | H | H | mp. 31–35° C. |
| 59 | 5-chloro-2-methyl-thiophen-3-yl | $CH_3$ | $CH_3$ | H | H | H | H | |
| 60 | 2-chloro-4,5-dimethyl-thiophen-3-yl | $CH_3$ | $CH_3$ | H | H | H | H | mp. 75–82° C. |
| 61 | 2,5-dimethyl-thiophen-3-yl | H | H | H | H | H | h | mp. 70–74 |
| 62 | 2,5-dimethyl-thiophen-3-yl | $CH_3$ | $CH_3$ | H | H | H | H | oil |
| 63 | 4,5-dibromo-thiophen-2-yl | H | H | H | H | H | H | mp. 126–128° C. |
| 64 | 4,5-dibromo-thiophen-2-yl | $CH_3$ | $CH_3$ | H | H | H | H | mp. 98–100° C. |
| 65 | 2,5-dichloro-thiazol-4-yl | H | H | H | H | H | H | mp. 100–102° C. |
| 66 | 2,5-dichloro-thiazol-4-yl | $CH_3$ | $CH_3$ | H | H | H | H | oil |

TABLE I-continued
| Compound NO. | R¹ | R¹⁶ | R¹⁷ | R¹⁸ | R¹⁹ | R²⁰ | R²¹ | CHARACTERISING DATA |
|---|---|---|---|---|---|---|---|---|
| 67 | 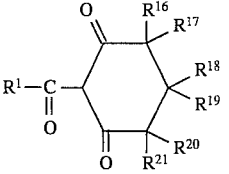 | H | H | H | H | H | H | mp. 135–145 |
| 68 | 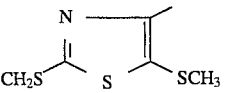 | H | H | H | H | H | H | mp. 104–106° C. |
| 69 | 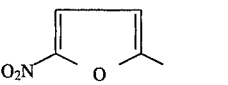 | CH₃ | CH₃ | H | H | H | H | mp. 60–65° C. |
| 70 | 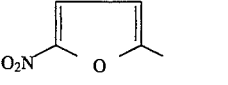 | H | H | H | H | H | H | mp. 94–104° C. |
| 71 | 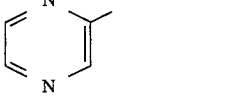 | CH₃ | CH₃ | H | H | H | H | mp. 89–93° C. |
| 72 | 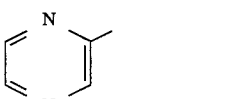 | H | H | H | H | H | H | ¹H NMR(CDCl₃): δ 2.06(t, CH₂); 2.42(t CH₂); 2.70(t, CH₂); 4.23(m, 2CH₂); 6.94(m, ar, H); 7.06(tr, s.OH) |
| 73 | 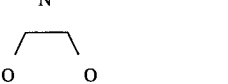 | H | H | H | H | H | H | mp. 80–82° C. |
| 74 | 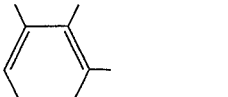 | H | H | H | H | H | H | mp. 156–7° C. |
| 75 |  | H | H | H | H | H | H | mpt. 139–140° C. |
| 76 | 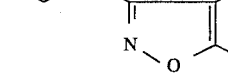 | H | H | H | H | H | H | mpt. 143–144° C. |

TABLE I-continued

Structure:

R¹−C(=O)− attached to a cyclohexane-1,3-dione ring with substituents R¹⁶, R¹⁷ (adjacent to one C=O), R¹⁸, R¹⁹, R²⁰, R²¹ on the ring carbons.

| Compound NO. | R¹ | R$^{16}$ | R$^{17}$ | R$^{18}$ | R$^{19}$ | R$^{20}$ | R$^{21}$ | CHARACTERISING DATA |
|---|---|---|---|---|---|---|---|---|
| 77 | 2-benzoxazolyl | H | H | H | H | H | H | mpt. 105–106° C. |

TABLE II

Structure: cyclohexane-1,3,5-trione with R² and R³ on one ring carbon, R⁶ and R⁷ on another, and an R¹−C(=O)− substituent.

| COMPOUND NO. | R¹ | R² | R³ | R⁶ | R⁷ | CHARACTERISING DATA |
|---|---|---|---|---|---|---|
| 78 | 1-methyl-5-trifluoromethyl-pyrazol-4-yl (with 3-CH₃) | $CH_3$ | $CH_3$ | $CH_3$ | $CH_3$ | mpt. 103–105° C. |
| 79 | 6-nitro-5-methyl-1,3-benzodioxol-yl | $CH_3$ | $CH_3$ | $CH_3$ | $CH_3$ | mpt. 90–93° C. |
| 80 | 2-methyl-4-(1-methylethylidene)-thiazol-5-yl | $CH_3$ | $CH_3$ | $CH_3$ | $CH_3$ | Oil $^1$H NMR 270 MHz, CDCl$_3$) δ 1.34(s, 6H); 1.47 (s, 6H); 2.64 (s, 3H); 2.70(s, 3H) |
| 81 | 2-(thien-2-yl)thiazol-4-yl | $CH_3$ | $CH_3$ | $CH_3$ | $CH_3$ | Oil ir (nujol) 1720, 1670, 1560 cm$^{-1}$ |
| 82 | 2,3-(methylenedioxy)phenyl derivative | $CH_3$ | $CH_3$ | $CH_3$ | $CH_3$ | mpt. 90–93° C. |

Compounds of formula (I) can be prepared by rearrangement of a compound of formula (II):

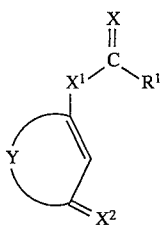

(II)

wherein $R^1$, X, $X^1$, $X^2$ and Y are as defined in relation to formula (I) in the presence of a cyanide source and a moderate base.

The reaction is suitably carried out in an inert organic solvent such as acetonitrile and at a temperature of from −30° C. to 90° C., preferably at from 20° C.–40° C.

Suitable cyanide sources are alkali metal cyanides such as sodium and potassium cyanide; cyanohydrins of methyl alkyl ketones having from 1–4 carbon atoms in the alkyl groups, such as acetone or methyl isobutyl ketone cyanohydrins; cyanohydrins of benzaldehyde or of $C_2$–$C_5$ aliphatic aldehydes such as acetaldehyde, propionaldehyde, etc., cyanohydrins; zinc cyanide; tri(lower alkyl) silyl cyanides, notably trimethyl silyl cyanide; and hydrogen cyanide itself.

A preferred cyanide source is acetone cyanohydrin.

The amount of the cyanide source employed is sufficient to catalyse the reaction, for example from 1–50 mole percent of the compound of formula (II), preferably from 1 to 10 mole percent.

Moderate bases suitable for use in this reaction include both organic bases such as tertiary amines and inorganic bases such as alkali metal carbonates and phosphates. Suitable tertiary amines include trialkylamines such as triethylamine, trialkanolamines such as triethanolamine, and pyridine. Suitable inorganic bases include potassium carbonate and trisodium phosphate.

Suitably the base is used in an amount of from about 1 to about 4 moles per mole of compound of formula (II), preferably about 2 moles per mole.

Compounds of formula (II) can be prepared by reacting a compound of formula (III):

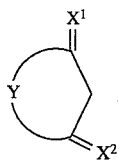

(III)

wherein $X^1$, $X^2$, and Y are as defined in relation to formula (I) with a compound of formula (IV):

$R^1CXZ$ (IV)

wherein $R^1$ and X are as defined in relation to formula (I) and Z is a leaving group, in the presence of a base.

Suitable bases for use in the reaction are the moderate bases described above for use in the rearrangement of the compound of formula (II). A preferred base is triethylamine.

Suitable leaving groups Z include halide such as chloride.

The reaction is suitably carried out in an inert organic solvent such as dichloromethane, 1,2-dichloroethane, toluene, acetonitrile, or dimethylformamide at moderate temperatures of from 0° C. to 50° C., conveniently at room temperature.

Compounds of formula (II) may also be prepared by reacting a compound of formula (III) with an acid of formula (V):

$R^1CXOH$ (V)

wherein $R^1$ and X are as defined in relation to formula (I), in the presence of a dehydrating agent and a basic organic catalyst.

Suitable dehydrating agents include dicyclohexyl-carbodiimide (DCC) which is employed in an amount of at least one molar equivalent to the compounds of formulae (III) and (V).

Examples of suitable basic organic catalysts include 4-dimethylaminopyridine (DMAP) and 4-pyrrolidinopyridine (PPY).

The reaction is suitably carried out in an inert organic solvent such as acetonitrile, tetrahydrofuran, dichloromethane or 1,2-dichloroethane. Moderate temperatures for example from 0° C. to 40° C. can be employed, conveniently ambient temperature.

Alternatively a compound of formula (I) can be prepared by reacting a compound of formula (III) as hereinbefore defined with a compound of formula (VI):

$R^1CXCN$ (VI)

wherein $R^1$ and X are as hereinbefore defined, in the presence of a base and a Lewis acid.

Suitable bases are the moderate bases described above for use in the rearrangement of the compound of formula (II).

Suitable Lewis acids are zinc chloride and aluminium trichloride, preferably zinc chloride.

The reaction is carried out in an organic solvent such as acetonitrile or methylene chloride and at moderate temperatures of from −20° C. to +40° C.

Suitably both the zinc chloride and the base are present in a slight molar excess with respect to the compounds of formula (III) and (VI).

Compounds of formulae (III), (IV), (V) and (VI) are either known compounds or they can be prepared from known compounds by conventional methods.

For instance a particular example of a compound of formula (V) are compounds of formula (VA)

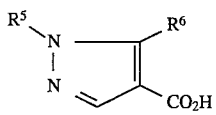

(VA)

wherein $R^5$ and $R^6$ are as defined above.

These compounds can be prepared as set out in Scheme A.

Scheme A

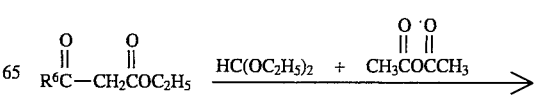

-continued
Scheme A

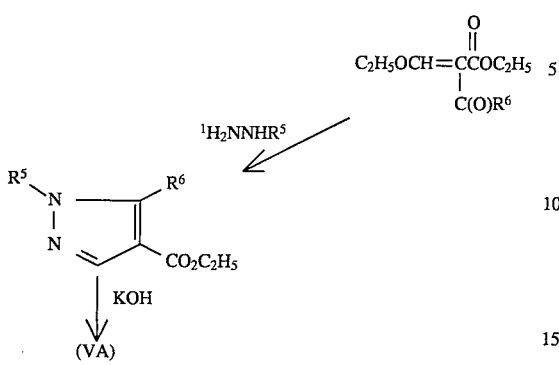

Suitable conditions for the first stage in Scheme A are found in an article, see R Jones *JACS*, 73 3686.

Conditions from the two subsequent steps are outlined in GB 2,149,402A.

A particular example of a compound of formula (III) is a compound of formula (IIIA):

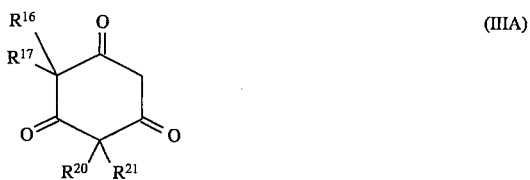

Compounds of formula (IIIA) wherein $R^{16}$, $R^{17}$, $R^{20}$ and $R^{21}$ are methyl or hydrogen and their preparation are described by Riedl and Risse (Justus Liebigs Annalen der Chemie, 1954, 585, 209).

Compounds of formula (IIIA) wherein $R^{16}$, R17, $R^{20}$ and $R^{21}$ are the same and are $C_{1-4}$ alkyl can be prepared by the following reaction Scheme B.

Scheme B

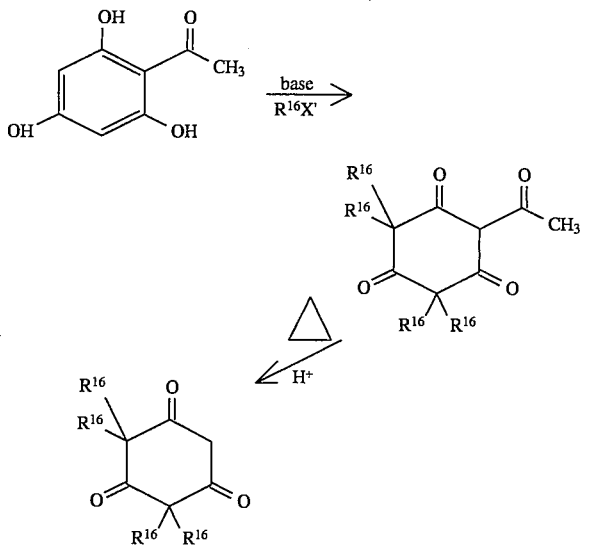

wherein X' is a leaving group such as halide, in particular iodide. Suitable reaction conditions will be apparent by analogy with the above-mentioned publication, For example, one suitable base for use in the first step in Scheme B is sodium methoxide in methanol. A suitable acid for use in second step of Scheme B is an inorganic acid such as hydrochloric acid.

By adjusting the conditions in the first step of the process, it may be possible to obtain compounds of formula (IIIA) wherein $R^{20}$ and/or $R^{21}$ are hydrogen.

Alternatively compounds of formula (IIIA) can be prepared using the methods described by Murin et al (Chem. Bet. 1959, 92, 2033) or methods analogous thereto.

In this way compounds of formula (IIIA) are prepared by cyclisation of a compound of formula (VII):

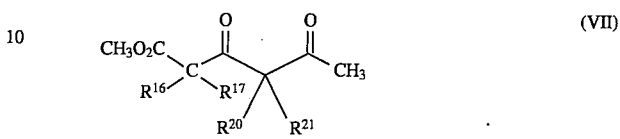

in the presence of a base such as sodium methoxide an organic solvent such as methanol. Compounds of formula (VII) can be prepared as outlined in Scheme C.

Scheme C

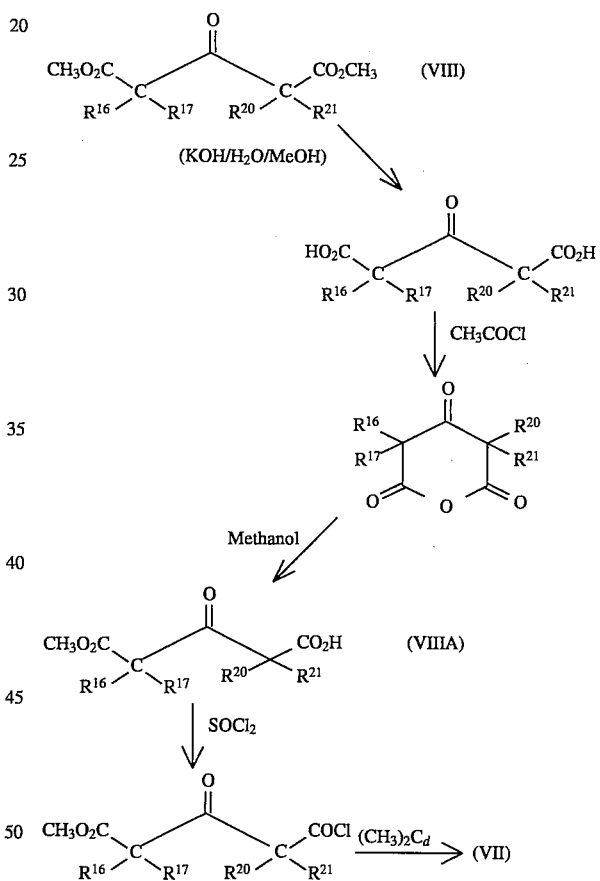

Precise reaction conditions for each step in Scheme B will depend upon the particular compounds involved and can be determined by routine procedures and the relevant literature.

Compounds of formula (VIII) can be prepared by the reaction of compounds of formula (IX):

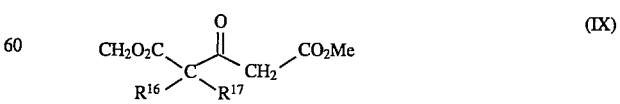

with a compound of formula $R^{20}X'$ and optionally thereafter with a compound of formula $R^{21}X'$ in the presence of a base such as sodium methoxide in an organic solvent such as methanol, wherein $R^{20}$, $R^{21}$ and X' are as hereinbefore defined.

When $R^{20}$ and $R^{21}$ are the same, then the reaction can be carried out in a single step. By controlling the reaction conditions, the extent of the reaction (i.e. whether one or both hydrogen atoms on the methylene are replaced by $R^{20}$) can be determined.

Compounds of formula (IX) can be prepared by reaction of a compound of formula (X):

wherein $R^{16}$ and $R^{17}$ are as hereinbefore defined, with (a) a strong base such as lithium diisopropyl-amide and (b) $CH_3O_2CCl$ under conventional reaction conditions.

Compounds of formula (X) can be prepared by reacting a compound of formula (XI):

with a compound of formula $R^{16}X'$ in the presence of a base; and optionally thereafter $R^{17}X'$ wherein $R^{16}$, $R^{17}$ and $X'$ are hereinbefore defined, as described above for the reaction of the compound of formula (IX).

Alternatively compounds of formula (IA) can be prepared by reacting a compound of formula (VIIIA) as set out in Scheme C with a compound of formula (XII):

wherein $R^1$ is as hereinbefore defined, in the presence of aluminium trichloride.

Reactions of this type are described by Merenyi and Nilson (Acta Chem. Scand, 1963, 17, 1801 and Acta Chem. Scand, 1964, 18, 1368).

Compounds of formula (XII) are known compounds or they can be prepared from known compounds by conventional methods.

Furthermore, compounds of formula (IA) wherein $R^{16}$, $R^{17}$, $R^{20}$ and $R^{21}$ are the same, can also be prepared by reacting a compound of formula (XIII):

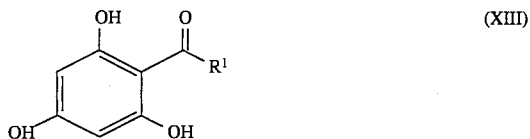

with a compound of formula $R^{16}X'$ in the presence of a base, wherein $R^1$, $R^{16}$ and $X'$ are as hereinbefore defined.

Suitable bases for use in the reaction are strong bases such as sodium methoxide.

The reaction is suitably carried out in an organic solvent such as methanol at temperatures of from 0° to 100° C.

The compounds of formula (I) are active as herbicides and therefore, in a further aspect the invention provides a process for severely damaging or killing unwanted plants which process comprises applying to the plants, or to the growth medium of the plants, an effective amount of a compound of formula (I) as hereinbefore defined.

The compounds of formula (I) are active against a broad range of weed species including monocotyledenous and dicotyledonous species. They may show some selectivity towards certain species, in particular maize.

The compounds of formula (I) may be applied directly to the plant (post-emergence application) or to the soil before the emergence of the plant (pre-emergence application).

The compounds of formulae (I) may be used on their own to inhibit the growth of, severely damage, or kill plants but are preferably used in the form of a composition comprising a compound of the invention in admixture with a carrier comprising a solid or liquid diluent.

Therefore, in yet a further aspect the invention provides plant growth inhibiting, plant damaging, or plant killing compositions comprising a compound of formula (I) as hereinbefore defined and an inert carrier or diluent.

Compositions containing compounds of formula (I) include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01 to 2% of active ingredient, while concentrated compositions may contain from 20 to 90% of active ingredient, although from 20 to 70% is usually preferred.

The solid compositions may be in the form of granules, or dusting powders wherein the active ingredient is mixed with a finely divided solid diluent, e.g., kaolin, bentonire, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-active agents may be of the cationic, anionic, or non-ionic type. The cationic agents are, for example, quaternary ammonium compounds (e.g. cetyltrimethylammonium bromide). Suitable anionic agents are soaps; salts or aliphatic mono ester of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl and triisopropylnaphthalenesulphonic acid. Suitable non-ionic agents are the condensation products of ethylene oxide with fatty alcohols such as oleyl alcohol and cetyl alcohol, or with alkylphenols such as octyl- or nonyl-phenol and octyl-cresol. Other non-ionic agents are the partial esters derived from long chain fatty acids and hexitol anhydrides, for example sorbitan monolaurate; the condensation products of the partial ester with ethylene oxide; and the lecithins.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene di-chloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredient(s) depending upon the intended purpose; amounts of 0.01% to 10.0% and preferably 0.1% to 2%, by weight of active ingredient(s) are normally used.

A preferred form of concentrated composition comprising the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties too, and increase the viscosity of the concentrate. Examples of preferred suspending agents include hydrated colloidal mineral silicates, such as montmorillonite, heidellite, nontronite, hectorite, saponite, and saucorite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited, the formulations selected for use and whether the compound is to be applied for foliage or root uptake. As a general guide, however, an application rate of from 0.005 to 20 kilograms per hectare is suitable while from 0.1 to 10 kilograms per hectare may be preferred.

The compositions of the invention may comprise, in addition to one or more compounds of the invention, one or more compounds not of the invention but which possess biological activity. Accordingly in yet a still further embodiment the invention provides a herbicidal composition comprising a mixture of at least one herbicidal compound of formula (I) as hereinbefore defined with at least one other herbicide.

The other herbicide may be any herbicide not having the formula (I). It will generally be a herbicide having a complementary action in the particular application. For example it may be desirable in certain circumstances to use the compound of formula (I) in admixture with a contact herbicide.

Examples of useful complementary herbicides include:

A. benzo-2,1,3-thiadiazin-4-one-2,2-dioxides such as 3-isopropylbenzo-2,1,3-thiadiazin-4-one-2,2-dioxide (bentazon);

B. hormone herbicides, particularly the phenoxy alkanoic acids such as 4-chloro-2-methylphenoxy acetic acid (MCPA), 2-(2,4-dichlorophenoxy)propionic acid (dichlorprop), 2,4,5-trichlorophenoxyacetic acid (2,4,5-T), 4-(4-chloro-2-methylphenoxy)butyric acid (MCPB), 2,4-dichlorophenoxyacetic acid (2,4-D), 4-(2,4-dichlorophenoxy)butyric acid (2,4-DB), 2-(4-chloro-2-methylphenoxy)propionic acid (mecoprop), and their derivatives (e.g. salts, esters and amides);

C. 3-[4-(4-halophenoxy)phenyl]-1,1-dialkylureas such as 3-[4-(4-chlorophenoxy)phenyl]-1,1-dimethylurea.

D. Dinitrophenols and their derivatives (e.g. acetates) such as 2-methyl-4,6-dinitrophenol (DNOC), 2-t-butyl-4,6-dinitrophenol (dinoterb), 2-secbutyl-4,6-dinitrophenol (dinoseb) and its ester, dinoseb acetate;

E. dinitroaniline herbicides such as N',N'-diethyl-2,6-dinitro-4-trifluoromethyl-m-phenylenediamine (dinitramine), 2,6-dinitro-N,N-dipropyl-4-trifluoromethylaniline (trifluralin) and 4-methylsulphonyl-2,6-dinitro-N,N-dipropylaniline (nittalin);

F. phenylurea herbicides such as N'-(3,4-dichlorophenyl)-N, N-dimethylurea (diuron) and N,N-dimethyl-N'-[3-(trifluoromethyl)phenyl]urea (flumeturon);

G. phenylcarbamoyloxyphenylcarbamates such as 3-[methoxy carbonylamino]phenyl (3-methylphenyl)carbamate (phenmedipham) and 3-[ethoxycarbonylamino]phenyl phenylcarbamate (desmedipham);

H. 2-phenylpyridazin-3-ones such as 5-amino-4-chloro-2-phenylpyridazin-3-one (pyrazon);

I. uracil herbicides such as 3-cyclohexyl-5,6-trimethyleneuracil (lenacil), 5-bromo-3-sec-butyl-6-methyl-uracil (bromacil) and 3-t-butyl-5-chloro-6-methyl-uracil (terbacil);

J. triazine herbicides such as 2-chloro-4-ethylamino-6-(i-propylamino)-1,3,5-triazine (atrazine), 2-chloro-4,6-di(ethylamino)-1,3,5-triazine (simazine) and 2-azido-4-(i-propylamino)-6-methylthio-1,3,5-triazine (aziprotryne);

K. 1-alkoxy-1-alkyl-3-phenylurea herbicides such as 3-(3,4-dichlorophenyl)-1-methoxy-1-methylurea (linuron), 3-(4-chlorophenyl)-1-methoxy-1-methylurea (monolinuron), 3-(4-bromo-4-chlorophenyl)-1-methoxy -1-methylurea (chlorobromuron).

L. thiolcarbamate herbicides such as S-propyl dipropylthiocarbamate (vernolate);

M. 1,2,4-triazin-5-one herbicides such as 4-amino-4,5-dihydro-3-methyl-6-phenyl-1,2,4-triazine-5-one (metamitron) and 4-amino-6-t-butyl-4,5-dihydro-3-methylthio-1,2,4-triazin-5-one (metribuzin);

N. benzoic acid herbicides such as 2,3,6-trichlorobenzoic acid (2,3,6-TBA), 3,6-dichloro-2-methoxybenzoic acid (dicamba) and 3-amino-2,5-dichlorobenzoic acid (chloramben);

O. anilide herbicides such as N-butoxymethyl-chloro-2',6'-diethylacetanilide (butachlor), the corresponding N-methoxy compound (alachlor), the corresponding N-i-propyl compound (propachlor), 3',4'-dichloropropionanilide (propanil) and 2-chloro-N-[pyrazol-1-ylmethyl]acet-2'-6'-xylidide (metazachlor);

P. dihalobenzonitrile herbicides such as 2,6-dichlorobenzonitrile (dichlobenil), 3,5-dibromo-4-hydroxybenzonitrile (bromoxynil) and 3,5-diiodo-4-hydroxybenzonitrile (ioxynil);

Q. haloalkanoic herbicides such as 2,2-dichloropropionic acid (dalapon), trichloroacetic acid (TCA) and salts thereof;

R. diphenylether herbicides such as 4-nitrophenyl 2-nitro-4-trifluoromethylphenyl ether (fluorodifen), methyl 5-(2, 4-dichlorophenoxy)-2-nitrobenzoate (befenox), 2-nitro-5-(2-chloro-4-trifluoromethylphenoxy) benzoic acid (acifluorfen) and salts and esters thereof, 2-chloro-4-trifluoromethylphenyl 3-ethoxy-4-nitrophenyl ether (oxyfluorfen) and 5-(2-chloro-4-(trifluoromethyl)phenoxy)-N-(methylsulfonyl) -2-nitrobenzamide (fomesafen); and S. phenoxyphenoxypropionate herbicides such as 2-(4-(4'-trifluoromethylphenoxy)-phenoxy)-propionic acid methylester (trifop-methyl), 2-(4-((5-trifluoromethyl)-2-(pyridinyl)oxy)phenoxypropanoic acid (fluazifop) and esters thereof, 2-(4-((3-chloro-5-trifluoromethyl) -2-pyridinyl)oxy)phenoxy)propanoic acid (haloxyfop) and esters thereof, 2-(4-((6-chloro-2-quinoxalinyl)oxy)phenoxypropanoic acid (xylofop) and esters thereof; and T. cyclohexanedione herbicides such as 2,2-dimethyl-4,6-dioxo-5-(1-((2-propenyloxy)amino)-butylidine) cyclohexane carboxylic acid (alloxydim) and salts thereof, 2-(1-ethoxyimino)butyl-5-(2-(ethylthio)-propyl)-3-hydroxy-2-cyclohexen-1-one (sethoxydim), 2-(1-(3-chloroallyloxyimino)butyl)-5-(2-ethylthio -propyl)-3-hydroxy cyclohex-2-enone (cloproxydim), (1-ethoxyimino)butyl)-

3-hydroxy-5-thian-3-yl cyclohex-2-enone (cycloxydim); and

U. sulfonyl urea herbicides such as 2-chloro-N-(4-methoxy-6-methyl-1,3,5-triazin-2-yl)-aminocarbonyl) benzenesulphonamide (chlorosulfuron), methyl 2-((((4,6-dimethyl-2 -pyrimidinyl)amino)carbonyl)amino)sulphonylbenzoic acid (sulfometuron), 2-(((3-(4-methoxy-6-methyl-1,3,5-triazin-2-yl)carbonyl)amino)sulphonyl)benzoic acid (metsulfuron) and esters thereof;

V. imidazolidinone herbicides such as 2-(4,5-dihydro-4-isopropyl-4-methyl-5-oxoimidazol-2-yl)quinoline-3-carboxylic acid (imazaquin), methyl 6-(4-isopropyl-4-methyl-5-oxo-2-imidazolin-2-yl)-m-toluate and p-toluate isomer (AC 222293)

W. arylanilide herbicides such as 1-methylethyl-N-benzoyl-N-(3-chloro-4-fluorophenyl)-L-alanine (flamprop-isopropyl), ethyl N-benzoyl-N-(3,4-dichloro-phenyl)-DL-alaninate (benzoylprop-ethyl), N-(2,4-difluorophenyl)-2-(3-(trifluoromethyl)phenoxy)-3-pyridinecarboxamide (diflufenican); and X. amino acid herbicides such as N-(phosphonomethyl)glycine (glyphosate) and DL-homoalanin-4-yl(methyl)phosphinic acid (phosphinothricin) and their salts and esters; and Y. organoarsenical herbicides such as monosodium methanearsonate (MSMA); and Z. miscellaneous herbicides including N,N-dimethyldiphenylacetamide (diphenamid), N-(1-naphthyl)phthalamic acid (naptalam) and 3-amino-1,2,4triazole, 2-ethoxy-2,3-dihydro-3,3-dimethylbenzofuran methanesulfonate (ethofumesate), 7-oxabicyclo (2.2.1) heptane. 1-Methyl-4-(1-methylethyl)-2-(2-methyl-phenylmethoxy)-exo (cinmethylin);

AA. Examples of useful contact herbicides include:

bipyridylium herbicides such as those in which the active entity is the 1,1'-dimethyl-4,4'-dipyridylium ion (paraquat) and those in which the active entity is the 1,1'-ethylene-2,2'-dipyridylium ion (diquat);

The following Examples illustrate the preparation of representative compounds of the invention.

EXAMPLE 1

This Example illustrates the preparation of Compound No. 1 in Table I.

To 2-thiophenecarboxylic acid chloride (1.2 ml) in dry dichloromethane (50 ml) was added Dimedone (1.57 g) and triethylamine (1.7 ml) dropwise. The reaction mixture was stirred at room temperature for 1½ hours and then evaporated to dryness to yield a soft solid (4.83 g). Dry acetonitrile (35 ml) was added to the solid which dissolved to form a yellow solution. Triethylamine (3.2 ml) and acetone cyanohydrin (6 drops) were added to the solution which was then stirred at room temperature for 2 hours. On purification by column chromatography using a silica column with an eluent consisting of hexane 50: ethyl acetate 50: acetic acid 1, the main orange band was collected and crystallised on standing to Compound No. 1 (97% yield).

EXAMPLE 2

This Example illustrates the preparation of Compound No. 2 in Table I.

A mixture of 2,5-dichlorothiophene acid chloride (1.06 g) and Dimedone (0.70 g) in dry acetonitrile (25 ml) was cooled in a water bath and triethylamine (0.76 ml) and acetonitrile (5 ml) added dropwise. The mixture was stirred at room temperature for ½ hour, triethylamine (1.4 ml) and acetonecyanohydrin (4 drops) added and stirring was continued for 20 hours, after which the solution was evaporated to dryness.

The residue was dissolved in ethyl acetate and the solution applied to a silica column using a eluent of hexane 50: ethylacetate 50: acetic acid 1 and the main orange band collected and solidified.

Further purification by recrystallisation from hexane and column chromatography as described above yielded Compound No. 2 (0.24 g).

EXAMPLE 3

This Example illustrates the preparation of Compound No. 5 in Table I.

5-Bromo-2-thiophenecarboxylic acid (2.09 g), dry dichloroethane (30 ml) and thionyl chloride (0.75 ml) were heated together at 80° C. for 4 hours. The mixture was cooled in an ice water Oath and Dimedone (1.40 g) added followed by the dropwise addition of triethylamine (2.8 ml) in dry dichloroethane (5 ml). After 1 hour at room temperature further triethylamine (2.8 ml) and acetonecyanohydrin (6 drops) were added and stirring continued for 15 hours. The solution was then left for a total of 3 days at room temperature, after which time it was evaporated to dryness, the residue dissolved in ethylacetate and the resulting suspension applied to a silica column and eluted with hexane 50: ethylacetate 50: acetic acid 1 and the main orange band collected which solidified to give Compound No. 5 as an orange solid (1.26 g).

EXAMPLE 4

This Example illustrates the preparation of Compound No. 6 in Table I.

5-Methyl-2-thiophenecarboxylic acid (0.71 g), cyclohexan-1,3-dione (0.5 g) and a small amount of (4-dimethylaminopyridine) (100 mgs) were dissolved in dry dichloromethane (20 ml) at 15° C. and dicyclohexylcarbodiimide (1.02 g) added. The reaction mixture was stirred at 18°–20° C. for 3–4 hours and then filtered and evaporated. To the resulting oil were added dry acetonitrile (8 ml), acetone cyanohydrin (4 drops) and triethylamine (1.4 ml) and the mixture stirred for 2–3 hours at room temperature and subsequently evaporated to dryness.

The residue was purified by column chromatography using as eluent, hexane 70: ethylacetate 30: acetic acid 3 and the main yellow band collected and evaporated to give Compound No. 6 as a cream solid (0.38 g).

EXAMPLE 5

This Example illustrates the preparation of compound 10 in Table 1.

5-Chloro-2-thienoyl chloride (8.0 g, 44 mmol) and 1.3-cyclohexanedione (5.0 g, 44 mmol) were dissolved in 150 ml of methylene chloride. Triethylamine (15 ml, 110 mmol) was added and the resulting mixture was stirred at room temperature for fifteen minutes. The solution was washed with dilute hydrochloric acid, 5% potassium carbonate and saturated sodium chloride, dried over anhydrous magnesium sulfate and concentrated in vacuum. The residue was dissolved in 100 ml of acetonitrile. Triethylamine (15 ml, 110 mmol) and acetone cyanohydrin (0.2 g) were added and the mixture stirred at room temperature for 2 hours. After dilution with ether, the solution was washed with dilute hydrochloric acid and extracted with 5% potassium carbonate. The basic extract was acidified with hydrochloric acid and extracted with ether. The ether extract was washed with saturated sodium chloride, dried over magnesium sulfate and concentrated in vacuum yielding 3.8 g of the desired product (mp. 31°–35° C.). It was identified as such by nuclear magnetic resonance spectroscopy, infrared spectroscopy and mass spectroscopy.

EXAMPLE 6

This Example illustrates the preparation of compound 42 in Table 1.

4-Carboxy-1-methyl-5-trifluoromethyl-1H-pyrazole (5.0 g, 26 mmol) was dissolved in a mixture of tetrahydrofuran (25 ml) and acetonitrile (25 ml). Dicyclohexylcarbodiimide (5.3 g, 26 mmol) was added and the resulting mixture was stirred at room temperature for 5 minutes. 1,3-Cyclohexanedione (2.9 g, 26 mmol) dissolved in a mixture of tetrahydrofuran (25 ml) and acetonitrile (25 ml) was added and the mixture stirred at room temperature overnight. The reaction mixture was filtered and the filtrate was concentrated in vacuum. The residue was dissolved in acetonitrile (100 ml). Triethylamine (9 ml, 66 mmol) and trimethylsilyl cyanide (0.2 g) were added and the mixture stirred at 50° C. for 4 hours. After dilution with ether, the solution was washed with dilute hydrochloric acid and extracted with 5% potassium carbonate. The basic extract was acidified with hydrochloric acid and extracted with ether. The ether extract was washed with saturated sodium chloride, dried over anhydrous magnesium sulfate and concentrated in vacuum yielding 2.7 g of the desired product as a yellow solid (mp. 118°–122° C.). It was identified as such by nuclear magnetic resonance spectroscopy, infrared spectroscopy and mass spectroscopy.

Compounds 7–71 and 78 were prepared by methods analogous to those employed in Examples 5 or 6.

EXAMPLE 7

This Example illustrates the preparation of compound 79 in Table II.

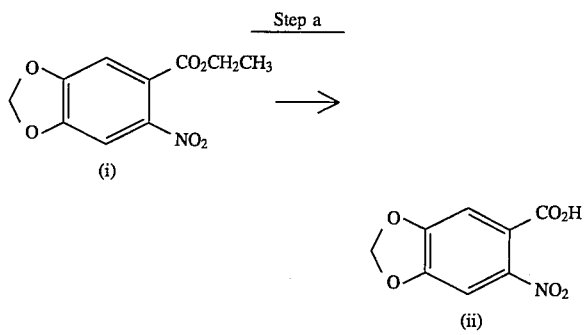

The ester (i) (4.17 g was dissolved in isopropylalcohol (50 ml) and sodium hydroxide (0.77 g) in water (5 ml) added with stirring. The mixture was heated under reflux for 2 hours, and then poured into 2M aqueous hydrochloric acid to quench the reaction. The product was then extracted into ethyl acetate and the extracts dried over magnesium sulphate. Concentration under reduced pressure gave the acid (ii) as a yellow solid.

Step b 2,2,4,4-Tetramethyl-cyclohexan-1,3,5-trione (0.50 g) and the acid from step (a)) (0.58 g) were stirred together in dry dichloromethane DMAP (ca 50 mg) and dicyclohexyl carbodiimide (0.47 g) were added and the mixture was allowed to stand to room temperature overnight. The reaction mixture was filtered and concentrated under reduced pressure to give a yellow solid. This solid was dissolved in acetonitrile and triethylamine (0.76 ml) added. Acetone cyanohydrin (4 drops) were added and the mixture stirred at room temperature for 5 hours. It was then poured into 2M aqueous hydrochloric acid, extracted with ethyl acetate, dried and concentrated under reduced pressure and recrystallised from ethanol/ethyl acetate to give compound 78 as a yellow crystalline solid (0.15 g).

EXAMPLE 8

This Example illustrates the preparation of compound 80 in Table 2.

Step a

Ethyl 2,4-dimethylthiazole-5-carboxylate (3.0 g, 0.016 mol) was dissolved in isopropyl alcohol (50 ml) and sodium hydroxide (0.71 g, 0.018 mol) in $H_2O$ (5 ml) added. The reaction mixture was stirred at room temperature for 1 hour then heated under reflux for 1 hour, poured into $H_2O$, acidified with 2M hydrochloric acid solution extracted with ethyl acetate. The aqueous phase was concentrated under reduced pressure, triturated with water, and filtered to give a pale pink solid (mpt. 200° C.).

Step b 2,2,4,4-Tetramethylcyclohexan-1,3,5-trione (0.50 g, 2.75 mmol) was dissolved in dichloromethane (30 ml) and the product from step (a), and DMAP (ca 50 mg) and dicyclohexylcarbodiimide (0.47 g) added. The reaction mixture was stirred at room temperature for 1 hour, and then filtered and concentrated under reduced pressure. The residue was dissolved in acetonitrile (30 ml) and triethylamine (0.76 ml) was added, together with acetone cyanohydrin (4 drops). The reaction mixture was stirred at room temperature for 2 hours and then heated under reflux for 1½ hours. Reaction mixture was then poured into 2M aqueous hydrochloric acid solution, extracted with ethyl acetate, dried and concentrated under reduced pressure to give a yellow oil and solid which was triturated repeatedly with $CH_2Cl_2$ to remove triketone starting material. Compound 80 was obtained as a yellow oil.

Compounds 72 and 83 were prepared by methods analogous to those described in Examples 7 and 8.

EXAMPLE 9

This Example illustrates the preparation of compound 80 in Table II.

Step a 5-(2-Pyridyl)thiophene-2-carboxylic acid (1.0 g) was stirred in toluene (50 ml) and dimethylformamide (3 drops). Thionyl chloride (1.6 ml, 9.76 mmol) was added and the reaction mixture stirred at room temperature for 6 hours, then heated under reflux for 1 hour and filtered. Concentration under reduced pressure gave a yellow solid (1.08 g).

Step b

Compound (iii) (0.50 g) and the acid chloride from step (a) (0.63 g), were stirred in dry acetonitrile (15 ml) at room temperature. Triethylamine (0.38 ml) was added, the cloudy yellow suspension changing to clear orange then to clear dark yellow as the triethylamine was added. The reaction mixture was then stirred at room temperature for 2 hours and triethylamine (0.76 ml) and acetone cyanohydrin (4 drops) were added. After stirring at room temperature for 6 hours the reaction mixture was poured into $H_2O$ (50 ml), acidified with 2M HCl (100 ml), extracted with EtOAc (100 ml), the EtOAc phase was washed with 50% $NA_2CO_3$ solution (100 ml) and the base layer then acidified with 2M HCl. The mixture was then extracted with $CH_2Cl_2$, and the $CH_2Cl_2$ phase washed with brine (25 ml), dried over $MgSO_4$, filtered and concentrated under reduced pressure to give a bright yellow solid.

Compound 81 was obtained by prep plate chromatography using the solvent system ethylacetate/hexane/acetic acid in the ratio 75:175:1. It was obtained as a yellow oil that crystallised on standing.

Compounds 73, 74, 75 and 76 were prepared by methods analogous to those described in Example 9.

EXAMPLE 10

This Example illustrates the preparation of compound 77.

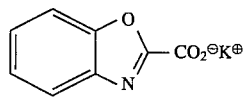 (v)

The salt (v) (0.84 g) was treated with toluene (35 ml) and DMF (5 drops) added. The stirred suspension was treated dropwise with oxalyl chloride (0.75 ml). This caused a colour change to purple and considerable effervescence. The mixture was stirred overnight at room temperature and then evaporated under reduced pressure to give an off white solid. This was treated with acetonitrile (15 ml) and partially dissolved. The mixture was stirred with ice-bath cooling and cyclohexane-1,3-dione (0.6 g) was added. Triethylamine (0.75 ml) was then added dropwise. Most of the precipitate dissolved. The mixture was stirred with continued cooling for 3 horus. Allowed to obtain room temperature and then treated with acetone cyanohydrin (6 drops). Triethylamine (1.8 ml) was then slowly added.

The mixture was then stirred at room temperature for 4 hours then left to stand over the weekend. A yellow and orange solution resulted. This was filtered and the filtrate poured into water (100 mls). The resulting alkaline solution was acidified with dilute HCl and became cloudy.

The mixture was extracted with dichloromethane to give a yellow organic layer. This was extracted with sodium carbonate solution and the aqueous layer acidified with dilute hydrochloric acid. The cloudy mixture formed was extracted with dichloromethane and the organic phase washed with water dried over magnesium sulphate and then filtered and evaporated to give a yellow oil which set on standing to give compound 77 as a yellow solid (0.59).

Biological Data

As previously mentioned, the herein described compounds produced in the above-described manner are phytotoxic compounds which are useful and valuable in controlling various plant species. Selected compounds of this invention were tested as herbicides in the following manner.

Pre-emergence herbicide test. On the day preceding treatment, seeds of seven different weed species are planted in loamy sand soil in individual rows using one species per row across the width of a flat. The seeds used are green foxtail (FT) (*Setaria viridis*), watergrass (WG) (*Echinochloa crusgalli*), wild oat (WO) (*Arena fatua*), annual morningglory (AMG) (*Ipomoea lacunosa*), velvetleaf (VL) (*Abutlion theophrasti*), Indian mustard (MD) (*Brassica juncea*), and yellow nutsedge (YNG) (*Cyperus esculentus*). Ample seeds are planted to give about 20 to 40 seedlings per row, after emergence, depending upon the size of the plants.

Using an analytical balance, 600 milligrams (mg) of the compound to be tested are weighed out on a piece of glassine weighing paper. The paper and compound are placed in a 60 milliliter (ml) wide-mouth clear bottle and dissolved in 45 ml of acetone or substituted solvent. Eighteen ml of this solution are transferred to a 60 ml wide-mouth clear bottle and diluted with 22 ml of a water and acetone mixture (19:1) containing enough polyoxyethylene sorbitan monolaurate emulsifier to give a final solution of 0.5% (v/v). The solution is then sprayed on a seed flat on a linear spray table calibrated to deliver 80 gallons per acre (748 L/ha). The application rate is 4 lb/acre (4.48 Kg/ha).

After treatment, the flats ace placed in the greenhouse at a temperature of 70° to 80° F. and watered by sprinkling. Two weeks after treatment, the degree of injury or control is determined by comparison with untreated check plants of the same age. The injury rating from 0 to 100% is recorded for each species as percent control with 0% representing no injury and 100% representing complete control.

Post Emergence Test

Post emergence results were obtained using similar methods except that the compounds were applied to the young plants.

The results of the tests are shown in the following Tables III and IV.

TABLE III

| Compound | Pre-emergence Herbicidal Activity Application Rate 4.00 lb/ac | | | | | | |
|---|---|---|---|---|---|---|---|
| No. | FT | WG | WO | AMG | VL | MD | YNG |
| 4 | 0 | 0 | 0 | 0 | 100 | 10 | 35 |
| 6 | 25 | 20 | 0 | 0 | 0 | 0 | 0 |
| 7 | 8 | 0 | 5 | 0 | 10 | 70 | 70 |
| 11 | 20 | 0 | 0 | 0 | 25 | 60 | 0 |
| 12 | 20 | 25 | 0 | 0 | 0 | 25 | 0 |
| 14 | 0 | 0 | 0 | 5 | 0 | 20 | 0 |
| 16 | 0 | 0 | 0 | 0 | 85 | 25 | 70 |
| 18 | 50 | 35 | 0 | 0 | 100 | 10 | 0 |
| 19 | 60 | 0 | 0 | 0 | 20 | 100 | 25 |
| 20 | 30 | 25 | 0 | 25 | 100 | 95 | 30 |
| 21 | 0 | 0 | 0 | 0 | 100 | 100 | 30 |
| 22 | 0 | — | 25 | 0 | 0 | 0 | 0 |
| 23 | 25 | 40 | 20 | 0 | 0 | 0 | 0 |
| 29 | 70 | 100 | 95 | 30 | 95 | 100 | 80 |
| 30 | 100 | 100 | 80 | 85 | 100 | 100 | 80 |
| 31 | 0 | 10 | 0 | 0 | 10 | 40 | 80 |
| 32 | 0 | 0 | 0 | 0 | 0 | 0 | 80 |
| 33 | 0 | 0 | 0 | 0 | 0 | 0 | 30 |
| 35 | 0 | 30 | 0 | 0 | 30 | 0 | 30 |
| 36 | 0 | 0 | 30 | 80 | 90 | 10 | 0 |
| 37 | 30 | 0 | 0 | 0 | 0 | 0 | 0 |
| 38 | 0 | 0 | 0 | 0 | 5 | 0 | 0 |
| 40 | 80 | 50 | 30 | 10 | 50 | 50 | 70 |
| 41 | 90 | 100 | 20 | 30 | 100 | 95 | 80 |
| 42 | 100 | 50 | 100 | 100 | 100 | 95 | 80 |
| 43 | 90 | 30 | 90 | 100 | 100 | 60 | 80 |

TABLE III-continued

| Compound No. | Pre-emergence Herbicidal Activity Application Rate 4.00 lb/ac | | | | | | |
|---|---|---|---|---|---|---|---|
| | FT | WG | WO | AMG | VL | MD | YNG |
| 44 | 90 | 85 | 20 | 100 | 100 | 5 | 80 |
| 45 | 100 | 100 | 20 | 100 | 100 | 90 | 80 |
| 46 | 20 | 85 | 20 | 100 | 100 | 60 | 80 |
| 47 | 30 | 80 | 0 | 100 | 100 | 80 | 80 |
| 48 | 80 | 80 | 0 | 100 | 100 | 20 | 70 |
| 49 | 100 | 20 | 100 | 100 | 100 | 90 | 80 |
| 50 | 60 | 90 | 0 | 100 | 100 | 95 | 80 |
| 51 | 100 | 90 | 30 | 100 | 100 | 40 | 30 |
| 52 | 100 | 95 | 60 | 100 | 90 | 75 | 70 |
| 53 | 80 | 70 | 20 | 100 | 100 | 10 | 0 |
| 54 | 100 | 80 | 20 | 100 | 60 | 100 | 0 |
| 55 | 100 | 70 | 30 | 98 | 90 | 85 | 20 |
| 56 | 95 | 70 | 20 | 80 | 95 | 75 | 60 |
| 57 | 100 | 90 | 20 | 95 | 95 | 75 | 80 |
| 60 | 20 | 25 | 0 | 0 | 0 | 0 | 0 |
| 65 | 30 | 0 | 0 | 0 | 0 | 0 | 0 |
| 66 | 0 | — | 25 | 0 | 0 | 0 | 0 |
| 69 | 25 | 40 | 20 | 0 | 0 | 0 | 0 |
| 78 | 100 | 100 | 90 | 100 | 90 | 90 | 80 |

Compounds 13, 15, 24, 25, 26, 27, 28, 34, 39 showed no pre-emergence activity against the test species at the given rate of application.

TABLE IV

| Compound No. | Post-emergence Herbicidal Activity Application Rate 4.00 lb/ac | | | | | | |
|---|---|---|---|---|---|---|---|
| | FT | WG | WO | AMG | VL | MD | YNG |
| 4 | 40 | 25 | 0 | 85 | 100 | 100 | 40 |
| 6 | 20 | 30 | 0 | 25 | 70 | 50 | 0 |
| 7 | 0 | 30 | 0 | 10 | 0 | 10 | 0 |
| 9 | 40 | 30 | 10 | 0 | 100 | 95 | 0 |
| 10 | 0 | 30 | 0 | 0 | 0 | 40 | 0 |
| 11 | 20 | 30 | 0 | 35 | 20 | 30 | 0 |
| 12 | 0 | 0 | 0 | 0 | 25 | 25 | 0 |
| 13 | 10 | 20 | 0 | 0 | 15 | 25 | 0 |
| 14 | 0 | 0 | 0 | 15 | 0 | 20 | 0 |
| 15 | 0 | 0 | 0 | 20 | 20 | 80 | 0 |
| 16 | 0 | 0 | 0 | 0 | 60 | 100 | 80 |
| 18 | 0 | 20 | 10 | 100 | 100 | 90 | 35 |
| 19 | 0 | 0 | 0 | 25 | 60 | 100 | 70 |
| 20 | 20 | 0 | 0 | 25 | 100 | 100 | 0 |
| 21 | 0 | 25 | 0 | 40 | 70 | 80 | 0 |
| 22 | 0 | 20 | 0 | 0 | 0 | 35 | 0 |
| 24 | 20 | 0 | — | 30 | 20 | 40 | 0 |
| 25 | 20 | 25 | 0 | 0 | 35 | 50 | 15 |
| 26 | 0 | 0 | 0 | 0 | 0 | 0 | 20 |
| 28 | 0 | 40 | 0 | 20 | 40 | 80 | 0 |
| 29 | 65 | 80 | 80 | 10 | 90 | 80 | 50 |
| 30 | 80 | 80 | 40 | 30 | 30 | 50 | 80 |
| 31 | 0 | 50 | 0 | 5 | 80 | 80 | 60 |
| 32 | 0 | 0 | 0 | 0 | 50 | 50 | 30 |
| 33 | 0 | 0 | 0 | 5 | 30 | 0 | 10 |
| 35 | 0 | 30 | 0 | 0 | 10 | 10 | 0 |
| 36 | 10 | 10 | 80 | 100 | 100 | 100 | 70 |
| 40 | 80 | 50 | 30 | 10 | 50 | 50 | 70 |
| 41 | 60 | 90 | 80 | 20 | 100 | 80 | 70 |
| 42 | 100 | 90 | 80 | 100 | 100 | 90 | 80 |
| 43 | 90 | 85 | 50 | 100 | 100 | 100 | 70 |
| 44 | 10 | 20 | 10 | 10 | 90 | 80 | 30 |
| 45 | 85 | 90 | 90 | 100 | 90 | 90 | 75 |
| 46 | 20 | 40 | 10 | 90 | 80 | 20 | 70 |
| 47 | 10 | 40 | 0 | 80 | 80 | 60 | 70 |
| 48 | 5 | 40 | 0 | 100 | 95 | 30 | 60 |
| 49 | 30 | 70 | 5 | 60 | 60 | 20 | 80 |
| 50 | 20 | 60 | 5 | 60 | 60 | 40 | 80 |
| 51 | 30 | 40 | 20 | 80 | 100 | 25 | 0 |
| 52 | 50 | 60 | 50 | 85 | 90 | 40 | 30 |
| 53 | 10 | 10 | 0 | 80 | 80 | 5 | 0 |
| 54 | 10 | 30 | 10 | 60 | 60 | 10 | 0 |
| 55 | 40 | 50 | 30 | 50 | 30 | 40 | 10 |
| 56 | 20 | 50 | 40 | 60 | 80 | 20 | 30 |
| 57 | 50 | 50 | 50 | 80 | 80 | 40 | 40 |
| 58 | 40 | 30 | 10 | 0 | 100 | 95 | 0 |
| 60 | 20 | 30 | 0 | 25 | 70 | 80 | 0 |
| 61 | 0 | 0 | 0 | 0 | 25 | 25 | 0 |
| 62 | 10 | 20 | 0 | 0 | 15 | 25 | 0 |
| 63 | 0 | 0 | 0 | 15 | 0 | 20 | 0 |
| 64 | 0 | 0 | 0 | 20 | 20 | 50 | 0 |
| 66 | 0 | 0 | 0 | 0 | 5 | 0 | 0 |
| 70 | 40 | 35 | 20 | 15 | 70 | 60 | 20 |
| 71 | 50 | 60 | 0 | 15 | 10 | 40 | 10 |
| 78 | 85 | 80 | 80 | 80 | 85 | 70 | 80 |

GLASSHOUSE TESTS FOR HERBICIDAL ACTIVITY

The compounds were applied to the following species Lettuce (LT), Tomato (TO), *Arena fatua* (Av) and *Setaria viridis* (St) using a travelling boom track sprayer at a volume equivalent to 1000 l ha$^{-1}$ and at concentrations corresponding to application rates 10 kg ha$^{-1}$. Assessments were made for pre-emergence activity 17–20 days after direct spraying onto the seed, the seed having been covered with a compost for that period. Assessments were also made for post-emergence activity 13 days after spraying onto young plants.

The assessment scale used was as follows:

0=0–25% damage
1=26–50% damage
2=51–75% damage
3=76–100% damage

The results of this test are shown in Table V.

TABLE V

| COMPOUND NO. | PRE OR POST EMERGENCE APPLICATION | DAYS AFTER TEST | TEST PLANTS 4 | | | |
|---|---|---|---|---|---|---|
| | | | Lt | To | Av | St |
| 72 | Post | 13 | 3 | 3 | 3 | 3 |
| | Pre | 17 | 3 | 3 | 0 | 2 |
| 73 | Post | 13 | 3 | 3 | 3 | 3 |
| | Pre | 20 | 3 | 3 | 3 | 3 |
| 76 | Post | 13 | 0 | 0 | 0 | 0 |
| | Pre | 20 | 0 | 0 | 0 | 0 |
| 75 | Post | 13 | 2 | 1 | 0 | 0 |
| | Pre | 20 | 3 | 2 | 0 | 0 |
| 79 | Post | 13 | 3 | 3 | 3 | 3 |
| | Pre | 20 | 3 | 3 | 3 | 3 |
| 80 | Post | 13 | 3 | 3 | 3 | 3 |
| | Pre | 20 | 3 | 3 | 3 | 3 |
| 82 | Post | 13 | 3 | 3 | 2 | 3 |
| | Pre | 17 | 3 | 3 | 2 | 3 |
| 81 | Post | 13 | 0 | 0 | 0 | 0 |
| | Pre | 17 | 0 | 0 | 0 | 0 |
| 77 | Post | 13 | 3 | 3 | 1 | 1 |
| | Pre | 17 | 3 | 3 | 0 | 0 |
| 78 | Post | 13 | 3 | 3 | 0 | 0 |
| | Pre | 20 | 3 | 3 | 0 | 0 |

The herbicidal activity of the others of compounds was tested as follows:

Each compound in the appropriate concentration was incorporated into a 4% emulsion of methyl cyclohexanone and a 0.4% blend of 3.6 parts Tween 20 and 1 part Span 80. Tween 20 is a Trade Mark for a surface active agent comprising a condensate of 20 molar proportions of ethylene oxide with sorbitan laurate. Span 80 is a Trade Mark for a surface-active agent comprising sorbitan monolaurate. Formulation was effected by dissolving the compound in the requisite amount of solvent/surfactant blend. If necessary glass beads were added, the total liquid volume adjusted to 5 ml with water and the mixture shaken to effect complete dissolution of the compound. The formulation so prepared, after removal of beads where necessary, was then diluted to final spray volume (45 ml) with water.

The spray compositions so prepared were sprayed onto young pot plants (post-emergence test) at a rate equivalent to 1000 liters per hectare. Damage to plants was assessed 13 days after spraying by comparison with untreated plants, on a scale of 0 to 5 where 0 is 0–10% damage, 1 is 11 to 25% damage, 2 is 26–50% damage, 3 is 51–80% damage, 4 is 81–95% damage and 5 is 96–100% damage.

In a test carried out to detect pre-emergence herbicidal activity, seeds of the test species were placed on the surface of plastic trays of compost and sprayed with the compositions at the rate of 1000 liters per hectare. The seeds were then covered with further compost. 20 days after spraying, the seedlings in the sprayed plastic trays were compared with the seedlings in unsprayed control trays, the damage being assessed on the same scale of 0 to 5.

The results of the tests are given in Table VI below.

Am—*Amaranthus retroflexus*
Pi—*Polygonum aviculare*
Ca—*Chenopodium album*
Ga—*Galium aDarine*
Xa—*Xanthium spinosum*
Xs—*Xantbium strumarium*
Ab—*Abutilon theophrasti*
Co—*Cassia obtusifolia*
Av—*Avena fatua*
Dg—*Digitaria sanguinalis*
Al—*Alopecurus myosuroides*
St—*Setaria viridis*
Ec—*Echinchloa crus-galli*
Sh—*Sorghum halepense*
Ag—*Agropyron repens*
Cn—*cyperus rotundus*

We claim:

1. A compound of formula (I):

or an agriculturally acceptable salt, enamine, acrylate, sulphonate, carbamate or ether derivative thereof; wherein X,

TABLE VI

| COMPOUND NO. | RATE OF APPLICATION kg/1ha | PRE- OR POST-EMERGENCE APPLICATION | TEST PLANTS (see Table VII) | | | | | | | | | | | |
|---|---|---|---|---|---|---|---|---|---|---|---|---|---|---|
| | | | Sb | Rp | Ct | Sy | Mz | Ww | Rc | Bd | Ip | Am | Pi | Ca |
| 4 | 4 | Pre | 3 | 1 | — | 0 | 1 | 0 | 0 | 1 | 0 | 0 | 1 | 3 |
| | | Post | 3 | 3 | 3 | 2 | 3 | 2 | 0 | 3 | 3 | 4 | 3 | 4 |
| 3 | 4 | Pre | 3 | 3 | 1 | 0 | 0 | 0 | 0 | 0 | — | 0 | — | 0 |
| | | Post | 2 | 3 | 2 | 2 | 3 | 2 | 1 | 1 | 1 | 4 | 1 | 3 |
| 5 | 4 | Pre | 4 | 0 | 1 | 2 | 1 | 0 | 1 | 2 | 0 | 1 | 0 | 3 |
| | | Post | 1 | 0 | 0 | 0 | 0 | 0 | 0 | 1 | 0 | 0 | 0 | 0 |
| | | | Ga | Xa | Xs | Ab | Co | Av | Dg | Al | St | Ec | Sh | Ag | Cn |
| 4 | 4 | Pre | 0 | 3 | — | 5 | 0 | 0 | 0 | 0 | .1 | 0 | 0 | 0 | 3 |
| | | Post | 0 | — | 3 | 3 | 3 | 2 | 4 | 2 | 3 | 3 | 2 | 1 | 1 |
| 3 | 4 | Pre | 0 | 2 | — | 2 | 0 | 0 | 0 | 0 | 3 | 0 | 2 | 0 | 2 |
| | | Post | 1 | — | 1 | 2 | 2 | 0 | 3 | 1 | 0 | 2 | 2 | 2 | 0 |
| 5 | 4 | Pre | 1 | 2 | — | 3 | 2 | 0 | 0 | 0 | 0 | 0 | 0 | 0 | 0 |
| | | Post | 0 | — | 0 | 0 | 0 | 0 | 0 | 0 | 0 | 0 | 0 | 0 | 0 |

TABLE VII

Abbreviations Used for Test Plants

Sb—Sugar beet
Rp—Rape
Ct—Cotton
Sy—Soybean
Mz—Maize
Ww—Winter wheat
Rc—Rice
Bd—*Bidens pilosa*
Ip—*Ipomoea purpurea*

$X^1$ and $X^2$ are independently oxygen or sulphur, $R^1$ is a thienyl, furyl, indolyl or benzothienyl group, and Y is a $C_2$-$C_4$ alkylene group which is optionally substituted by oxo, mercapto, halo, nitro, cyano, amino, mono- or dialkylamino, amido, alkyl, alkenyl, alkynyl, cycloalkyl, haloalkyl, haloalkoxy phenyl, naphthyl, hydroxy, alkoxy, alkoxycarbonyl, alkylcarbonyl, mono- or dialkylcarbamoyl, alkythio, alkylsulphinyl, alkylsulphonyl, sulphonamido, alkylcarbonyloxy, alkyl carbonylamino, pyridyl or thienyl and which may also have a single hetero atom optionally interposed between adjacent carbons of the alkylene group, said hetero atom being an oxygen atom, a sulphur atom in a group

or an optionally alkyl- or alkoxy-substituted nitrogen atom, wherein p is 0, 1 or 2.

2. A compound according to claim 1 wherein $R^1$ is selected from

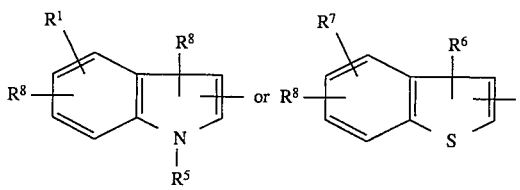

wherein $R^5$ is hydrogen or $C_1C_4$ alkyl or phenyl; $R^6$, $R^7$ and $R^8$ independently are (1) hydrogen; (2) halogen; (3) $C_1$–$C_4$ alkyl; (4) haloalkoxy; (5) $C_1$–$C_4$ alkoxy; (6) cyano; (7) nitro; (8) $C_1$–$C_4$ haloalkyl; (9) $R^9$ SOn— wherein n is the integer (a) $C_1$–$C_4$ alkyl;
 (b) $C_1$–$C_4$ alkyl substituted with halogen, cyano, $C_1$–$C_2$ alkoxy or $C_1$–$C_2$ alkylthio;
 (c) phenyl; or
 (d) benzyl; (10) —$NR^{10}R^{11}$ wherein $R^{10}$ and $R^{11}$ independently are hydrogen or $C_1$–$C_4$ alkyl; (11) $R^{12}C(O)$— wherein $R^{12}$ is $C_1$–$C_4$ alkyl or $C_1$–$C_4$ alkoxy; (12) —$SO_2NR^{10}R^{11}$ wherein $R^{10}$ and $R^{11}$ are as defined above; or (13) —$N(R^{10})C(O)R^{11}$ wherein $R^{10}$ and $R^{11}$ are as defined above.

3. A compound according to claim 1 wherein Y is

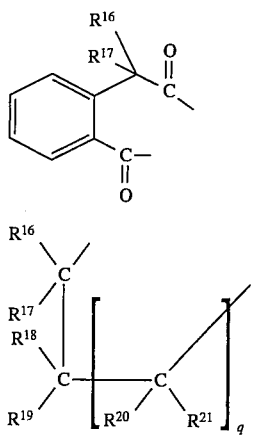

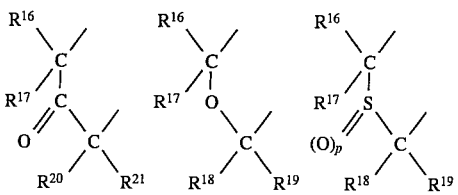

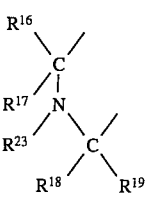

wherein $R^{16}$, $R^{17}$, $R^{18}$, $R^{19}$, $R^{20}$ and $R^{21}$ are independently selected from hydrogen, $C_{1-4}$ alkyl, $C_{1-4}$ alkanoyl or —$CO_2R^{22}$ wherein $R^{22}$ is $C_{1-4}$ alkyl or $R^{16}$ and $R^{17}$ or $R^{18}$ and $R^{19}$ or $R^{20}$ and $R^{21}$ together with the carbon atom to which they are attached form a $C_{3-6}$ cycloalkyl ring; q is 0 or 1; and $R^{23}$ is alkyl or alkoxy.

4. A compound according to claim 3 wherein $R^{16}$, $R^{17}$, $R^{18}$, $R^{19}$, $R^{20}$ and $R^{21}$ are hydrogen or methyl.

5. A compound according to claim 1 of formula (IA)

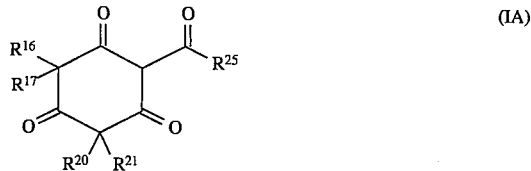

wherein $R^{16}$, $R^{17}$, $R^{20}$ and $R^{21}$ are hydrogen or methyl and $R^{25}$ is indolyl or benzothienyl.

6. A herbicidal composition comprising a compound of formula (I) as defined in claim 1 in combination with a carrier or diluent.

7. A method of killing or controlling unwanted plant species which method comprises applying to the plant or to the locus thereof a compound of formula (I) as defined in claim 1.

* * * * *